(12) United States Patent
Catanese, III et al.

(10) Patent No.: US 12,376,842 B2
(45) Date of Patent: Aug. 5, 2025

(54) FLEXIBLE SYSTEM FOR DELIVERING AN ANCHOR

(71) Applicant: Teleflex Life Sciences LLC, Wilmington, DE (US)

(72) Inventors: Joseph Catanese, III, Oakland, CA (US); Floria Cheng, San Francisco, CA (US); Theodore C. Lamson, Pleasanton, CA (US); Raul Macatangay, San Jose, CA (US); Matthew McLean, San Francisco, CA (US); Thomas C. Ryan, Livermore, CA (US); Ling-Kang Tong, Fremont, CA (US); Brian Y. Tachibana, Oakland, CA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 425 days.

(21) Appl. No.: 17/723,826

(22) Filed: Apr. 19, 2022

(65) Prior Publication Data

US 2022/0240921 A1 Aug. 4, 2022

Related U.S. Application Data

(63) Continuation of application No. 16/166,312, filed on Oct. 22, 2018, now Pat. No. 11,331,093, which is a
(Continued)

(51) Int. Cl.
*A61B 17/04* (2006.01)
*A61B 1/00* (2006.01)
(Continued)

(52) U.S. Cl.
CPC ...... *A61B 17/0401* (2013.01); *A61B 1/00148* (2022.02); *A61B 1/00183* (2013.01);
(Continued)

(58) Field of Classification Search
None
See application file for complete search history.

(56) References Cited

U.S. PATENT DOCUMENTS

| 659,422 A | 10/1900 | Shidler |
| 780,392 A | 1/1905 | Wanamaker et al. |

(Continued)

FOREIGN PATENT DOCUMENTS

| CA | 2477220 | 11/2007 |
| CN | 1697633 A | 11/2005 |

(Continued)

OTHER PUBLICATIONS

Final Office Action mailed Sep. 21, 2023, in co-pending U.S. Appl. No. 18/181,797.

(Continued)

*Primary Examiner* — Shaun L David
(74) *Attorney, Agent, or Firm* — Dorsey & Whitney LLP

(57) ABSTRACT

A system and associated method for manipulating tissues and anatomical or other structures in medical applications for the purpose of treating diseases or disorders or other purposes. In one aspect, the system includes a delivery device including a flexible portion that is suited to access target anatomy. The flexibility of an elongate portion of the delivery device can be varied. Additionally, the delivery device can include structure that maintains the positioning of the delivery device in patient anatomy.

20 Claims, 24 Drawing Sheets

Related U.S. Application Data continuation of application No. 13/538,758, filed on Jun. 29, 2012, now Pat. No. 10,130,353.

(51) Int. Cl.

| | | |
|---|---|---|
| *A61B 17/00* | (2006.01) | |
| *A61B 17/02* | (2006.01) | |
| *A61B 17/06* | (2006.01) | |
| *A61B 17/064* | (2006.01) | |
| *A61B 90/00* | (2016.01) | |

(52) U.S. Cl.
CPC .................. *A61B 17/0644* (2013.01); *A61B 2017/00274* (2013.01); *A61B 2017/003* (2013.01); *A61B 2017/00309* (2013.01); *A61B 2017/00314* (2013.01); *A61B 2017/00323* (2013.01); *A61B 2017/00557* (2013.01); *A61B 2017/00867* (2013.01); *A61B 2017/00871* (2013.01); *A61B 2017/00893* (2013.01); *A61B 2017/00964* (2013.01); *A61B 17/0218* (2013.01); *A61B 2017/0409* (2013.01); *A61B 2017/0419* (2013.01); *A61B 2017/0464* (2013.01); *A61B 2017/06052* (2013.01); *A61B 2017/0641* (2013.01); *A61B 2017/0645* (2013.01); *A61B 2017/0649* (2013.01); *A61B 2090/037* (2016.02)

(56) References Cited

U.S. PATENT DOCUMENTS

| | | |
|---|---|---|
| 789,467 A | 5/1905 | West |
| 2,360,164 A | 10/1944 | Frank |
| 2,485,531 A | 10/1949 | William et al. |
| 2,579,192 A | 12/1951 | Alexander |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Mckenzie |
| 3,326,586 A | 6/1967 | Frost et al. |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs et al. |
| 3,713,680 A | 1/1973 | Pagano |
| 3,716,058 A | 2/1973 | Tanner |
| 3,756,638 A | 9/1973 | Stockberger |
| 3,873,140 A | 3/1975 | Bloch |
| 3,875,648 A | 4/1975 | Bone |
| 3,886,933 A | 6/1975 | Mori et al. |
| 3,931,667 A | 1/1976 | Merser et al. |
| 3,976,079 A | 8/1976 | Samuels et al. |
| 4,006,747 A | 2/1977 | Kronenthal et al. |
| 4,137,920 A | 2/1979 | Bonnet |
| 4,164,225 A | 8/1979 | Johnson et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,419,094 A | 12/1983 | Patel |
| 4,452,236 A | 6/1984 | Utsugi |
| 4,493,323 A | 1/1985 | Albright et al. |
| 4,513,746 A | 4/1985 | Aranyi et al. |
| 4,621,640 A | 11/1986 | Mulhollan et al. |
| 4,655,771 A | 4/1987 | Wallsten |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,863,439 A | 9/1989 | Sanderson |
| 4,893,623 A | 1/1990 | Rosenbluth |
| 4,899,743 A | 2/1990 | Nicholson et al. |
| 4,926,860 A | 5/1990 | Stice et al. |
| 4,935,028 A | 6/1990 | Drews |
| 4,946,468 A | 8/1990 | Li |
| 4,955,859 A | 9/1990 | Zilber |
| 4,955,913 A | 9/1990 | Robinson |
| 4,968,315 A | 11/1990 | Gatturna |
| 4,994,066 A | 2/1991 | Voss |
| 5,002,550 A | 3/1991 | Li |
| 5,019,032 A | 5/1991 | Robertson |
| 5,041,129 A | 8/1991 | Hayhurst et al. |
| 5,046,513 A | 9/1991 | Gatturna et al. |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen et al. |
| 5,100,421 A | 3/1992 | Christoudias |
| 5,123,914 A | 6/1992 | Cope |
| 5,127,393 A | 7/1992 | McFarlin et al. |
| 5,129,912 A | 7/1992 | Noda et al. |
| 5,133,713 A | 7/1992 | Huang et al. |
| 5,159,925 A | 11/1992 | Neuwirth et al. |
| 5,160,339 A | 11/1992 | Chen et al. |
| 5,163,960 A | 11/1992 | Bonutti |
| 5,167,614 A | 12/1992 | Tessmann et al. |
| 5,192,303 A | 3/1993 | Gatturna et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,237,984 A | 8/1993 | Williams et al. |
| 5,254,126 A | 10/1993 | Filipi et al. |
| 5,258,015 A | 11/1993 | Li et al. |
| 5,267,960 A | 12/1993 | Hayman et al. |
| 5,269,802 A | 12/1993 | Garber |
| 5,269,809 A | 12/1993 | Hayhurst et al. |
| 5,300,099 A | 4/1994 | Rudie |
| 5,306,280 A | 4/1994 | Bregen et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,350,399 A | 9/1994 | Erlebacher et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,370,661 A | 12/1994 | Branch |
| 5,372,600 A | 12/1994 | Beyar et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,409,453 A | 4/1995 | Lundquist et al. |
| 5,411,520 A | 5/1995 | Nash et al. |
| 5,417,691 A | 5/1995 | Hayhurst |
| 5,435,805 A | 7/1995 | Edwards et al. |
| 5,441,485 A | 8/1995 | Peters |
| 5,458,612 A | 10/1995 | Chin |
| 5,464,416 A | 11/1995 | Steckel |
| 5,470,308 A | 11/1995 | Edwards et al. |
| 5,470,337 A | 11/1995 | Moss |
| 5,472,446 A | 12/1995 | Torre |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,759 A | 7/1996 | Kensey et al. |
| 5,531,763 A | 7/1996 | Mastri et al. |
| 5,534,012 A | 7/1996 | Bonutti |
| 5,536,240 A | 7/1996 | Edwards et al. |

(56) References Cited

U.S. PATENT DOCUMENTS

| | | |
|---|---|---|
| 5,540,655 A | 7/1996 | Edwards et al. |
| 5,540,701 A | 7/1996 | Sharkey et al. |
| 5,540,704 A | 7/1996 | Gordon et al. |
| 5,542,594 A | 8/1996 | McKean et al. |
| 5,545,171 A | 8/1996 | Sharkey et al. |
| 5,545,178 A | 8/1996 | Kensey et al. |
| 5,549,631 A | 8/1996 | Bonutti |
| 5,550,172 A | 8/1996 | Regula et al. |
| 5,554,162 A | 9/1996 | DeLange |
| 5,554,171 A | 9/1996 | Gatturna et al. |
| 5,562,688 A | 10/1996 | Riza |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,591,179 A | 1/1997 | Edelstein |
| 5,593,421 A | 1/1997 | Bauer |
| 5,611,515 A | 3/1997 | Benderev et al. |
| 5,620,461 A | 4/1997 | Moer et al. |
| 5,626,614 A | 5/1997 | Hart |
| 5,630,824 A | 5/1997 | Hart |
| 5,643,321 A | 7/1997 | McDevitt |
| 5,647,836 A | 7/1997 | Blake et al. |
| 5,653,373 A | 8/1997 | Green et al. |
| 5,665,109 A | 9/1997 | Yoon |
| 5,667,486 A | 9/1997 | Mikulich et al. |
| 5,667,488 A | 9/1997 | Lundquist et al. |
| 5,667,522 A | 9/1997 | Flomenblit et al. |
| 5,669,917 A | 9/1997 | Sauer et al. |
| 5,672,171 A | 9/1997 | Andrus et al. |
| 5,690,649 A | 11/1997 | Li |
| 5,690,677 A | 11/1997 | Schmieding et al. |
| 5,697,950 A | 12/1997 | Fucci et al. |
| 5,707,394 A | 1/1998 | Miller et al. |
| 5,716,368 A | 2/1998 | Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,749,889 A | 5/1998 | Bacich et al. |
| 5,752,963 A | 5/1998 | Allard et al. |
| 5,775,328 A | 7/1998 | Lowe et al. |
| 5,782,862 A | 7/1998 | Bonutti |
| 5,782,864 A | 7/1998 | Lizardi |
| 5,791,022 A | 8/1998 | Bohman |
| 5,800,445 A | 9/1998 | Ratcliff et al. |
| 5,807,403 A | 9/1998 | Beyar et al. |
| 5,810,848 A | 9/1998 | Hayhurst |
| 5,810,853 A | 9/1998 | Yoon |
| 5,814,072 A | 9/1998 | Bonutti |
| 5,830,179 A | 11/1998 | Mikus et al. |
| 5,830,221 A | 11/1998 | Stein et al. |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,908,447 A | 6/1999 | Schroeppel et al. |
| 5,919,198 A | 7/1999 | Graves et al. |
| 5,919,202 A | 7/1999 | Yoon |
| 5,921,982 A | 7/1999 | Lesh et al. |
| 5,921,986 A | 7/1999 | Bonutti |
| 5,928,252 A | 7/1999 | Steadman et al. |
| 5,931,844 A | 8/1999 | Thompson et al. |
| 5,941,439 A | 8/1999 | Kammerer et al. |
| 5,944,739 A | 8/1999 | Zlock et al. |
| 5,948,000 A | 9/1999 | Larsen et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Willard |
| 5,971,447 A | 10/1999 | Steck |
| 5,971,967 A | 10/1999 | Willard |
| 6,010,514 A | 1/2000 | Burney et al. |
| 6,011,525 A | 1/2000 | Piole |
| 6,015,428 A | 1/2000 | Pagedas |
| 6,024,751 A | 2/2000 | Lovato et al. |
| 6,030,393 A | 2/2000 | Corlew |
| 6,033,413 A | 3/2000 | Mikus et al. |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,053,935 A | 4/2000 | Brenneman et al. |
| 6,056,722 A | 5/2000 | Jayaraman |
| 6,056,772 A | 5/2000 | Bonutti |
| 6,066,160 A | 5/2000 | Colvin et al. |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,133 A | 9/2000 | Zappala |
| 6,117,160 A | 9/2000 | Bonutti |
| 6,117,161 A | 9/2000 | Li et al. |
| 6,120,539 A | 9/2000 | Eldridge et al. |
| 6,132,438 A | 10/2000 | Fleischman et al. |
| 6,139,555 A | 10/2000 | Hart et al. |
| RE36,974 E | 11/2000 | Bonutti |
| 6,143,006 A | 11/2000 | Chan |
| 6,152,935 A | 11/2000 | Kammerer et al. |
| 6,156,044 A | 12/2000 | Kammerer et al. |
| 6,156,049 A | 12/2000 | Lovato et al. |
| 6,159,207 A | 12/2000 | Yoon |
| 6,159,234 A | 12/2000 | Bonutti et al. |
| 6,193,714 B1 | 2/2001 | McGaffigan et al. |
| 6,200,329 B1 | 3/2001 | Fung et al. |
| 6,203,565 B1 | 3/2001 | Bonutti et al. |
| 6,206,895 B1 | 3/2001 | Levinson |
| 6,206,907 B1 | 3/2001 | Marino et al. |
| 6,228,096 B1 | 5/2001 | Marchand |
| 6,235,024 B1 | 5/2001 | Tu |
| 6,258,124 B1 | 7/2001 | Darois et al. |
| 6,261,302 B1 | 7/2001 | Voegele et al. |
| 6,261,320 B1 | 7/2001 | Tam et al. |
| 6,270,530 B1 | 8/2001 | Eldridge et al. |
| 6,280,441 B1 | 8/2001 | Ryan |
| 6,280,460 B1 | 8/2001 | Bolduc et al. |
| 6,287,317 B1 | 9/2001 | Makower et al. |
| 6,290,711 B1 | 9/2001 | Caspari et al. |
| 6,295,990 B1 | 10/2001 | Lewis et al. |
| 6,306,158 B1 | 10/2001 | Bartlett |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,382,214 B1 | 5/2002 | Raz et al. |
| 6,387,041 B1 | 5/2002 | Harari et al. |
| 6,398,795 B1 | 6/2002 | McAlister et al. |
| 6,398,796 B2 | 6/2002 | Levinson |
| 6,425,900 B1 | 7/2002 | Knodel et al. |
| 6,425,919 B1 | 7/2002 | Lambrecht |
| 6,428,538 B1 | 8/2002 | Blewett et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,672 B2 | 12/2002 | Slepian et al. |
| 6,491,707 B2 | 12/2002 | Makower et al. |
| 6,494,888 B1 | 12/2002 | Laufer et al. |
| 6,500,184 B1 | 12/2002 | Chan et al. |

(56) References Cited

U.S. PATENT DOCUMENTS

| | | |
|---|---|---|
| 6,500,195 B2 | 12/2002 | Bonutti |
| 6,506,190 B1 | 1/2003 | Walshe |
| 6,506,196 B1 | 1/2003 | Aufer |
| 6,514,247 B1 | 2/2003 | McGaffigan et al. |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,530,933 B1 | 3/2003 | Yeung et al. |
| 6,533,796 B1 | 3/2003 | Sauer et al. |
| 6,544,230 B1 | 4/2003 | Flaherty et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,582,453 B1 | 6/2003 | Tran et al. |
| 6,592,609 B1 | 7/2003 | Bonutti |
| 6,595,911 B2 | 7/2003 | LoVuolo |
| 6,596,013 B2 | 7/2003 | Yang et al. |
| 6,599,311 B1 | 7/2003 | Biggs et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | Goar et al. |
| 6,638,275 B1 | 10/2003 | McGaffigan et al. |
| 6,641,524 B2 | 11/2003 | Kovac |
| 6,641,592 B1 | 11/2003 | Sauer et al. |
| 6,656,182 B1 | 12/2003 | Hayhurst |
| 6,660,008 B1 | 12/2003 | Foerster et al. |
| 6,660,023 B2 | 12/2003 | McDevitt et al. |
| 6,663,589 B1 | 12/2003 | Halevy |
| 6,663,633 B1 | 12/2003 | Pierson |
| 6,663,639 B1 | 12/2003 | Laufer et al. |
| 6,699,263 B2 | 3/2004 | Cope |
| 6,702,846 B2 | 3/2004 | Mikus et al. |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,790,223 B2 | 9/2004 | Reever |
| 6,802,838 B2 | 10/2004 | Loeb et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,921,361 B2 | 7/2005 | Suzuki et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,986,784 B1 | 1/2006 | Weiser et al. |
| 6,988,983 B2 | 1/2006 | Connors et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,004,965 B2 | 2/2006 | Gross |
| 7,008,381 B2 | 3/2006 | Janssens |
| 7,011,688 B2 | 3/2006 | Gryska et al. |
| 7,015,253 B2 | 3/2006 | Escandon et al. |
| 7,041,111 B2 | 5/2006 | Chu |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,063,715 B2 | 6/2006 | Onuki et al. |
| 7,065,325 B2 | 6/2006 | Zegelin et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,096,301 B2 | 8/2006 | Beaudoin et al. |
| 7,104,949 B2 | 9/2006 | Anderson et al. |
| 7,105,004 B2 | 9/2006 | DiCesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas et al. |
| 7,226,558 B2 | 6/2007 | Nieman et al. |
| 7,232,448 B2 | 6/2007 | Battles et al. |
| 7,255,675 B2 | 8/2007 | Gertner et al. |
| 7,261,709 B2 | 8/2007 | Swoyer et al. |
| 7,261,710 B2 | 8/2007 | Elmouelhi et al. |
| 7,282,020 B2 | 10/2007 | Kaplan |
| 7,288,063 B2 | 10/2007 | Petros et al. |
| 7,303,108 B2 | 12/2007 | Shelton |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines |
| 7,335,197 B2 | 2/2008 | Sage et al. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,437,194 B2 | 10/2008 | Skwarek et al. |
| 7,463,934 B2 | 12/2008 | Tronnes et al. |
| 7,470,228 B2 | 12/2008 | Connors et al. |
| 7,481,771 B2 | 1/2009 | Fonseca et al. |
| 7,485,124 B2 | 2/2009 | Kuhns et al. |
| 7,553,317 B2 | 6/2009 | William et al. |
| 7,608,108 B2 | 10/2009 | Bhatnagar et al. |
| 7,632,297 B2 | 12/2009 | Gross |
| 7,645,286 B2 | 1/2010 | Catanese et al. |
| 7,658,311 B2 | 2/2010 | Boudreaux |
| 7,666,197 B2 | 2/2010 | Orban |
| 7,674,275 B2 | 3/2010 | Martin et al. |
| 7,682,374 B2 | 3/2010 | Foerster et al. |
| 7,695,494 B2 | 4/2010 | Foerster |
| 7,704,261 B2 | 4/2010 | Sakamoto et al. |
| 7,727,248 B2 | 6/2010 | Smith et al. |
| 7,731,725 B2 | 6/2010 | Gadberry et al. |
| 7,736,374 B2 | 6/2010 | Vaughan et al. |
| 7,758,594 B2 | 7/2010 | Lamson et al. |
| 7,766,923 B2 | 8/2010 | Catanese et al. |
| 7,766,939 B2 | 8/2010 | Yeung et al. |
| 7,780,682 B2 | 8/2010 | Catanese et al. |
| 7,780,687 B2 | 8/2010 | Heinrich et al. |
| 7,815,655 B2 | 10/2010 | Catanese et al. |
| 7,850,712 B2 | 12/2010 | Conlon et al. |
| 7,862,542 B1 | 1/2011 | Harmon |
| 7,862,584 B2 | 1/2011 | Lyons et al. |
| 7,887,551 B2 | 2/2011 | Bojarski et al. |
| 7,896,891 B2 | 3/2011 | Catanese et al. |
| 7,905,889 B2 | 3/2011 | Catanese et al. |
| 7,905,904 B2 | 3/2011 | Stone et al. |
| 7,909,836 B2 | 3/2011 | McLean et al. |
| 7,914,542 B2 | 3/2011 | Lamson et al. |
| 7,922,645 B2 | 4/2011 | Kaplan |
| 7,951,158 B2 | 5/2011 | Catanese et al. |
| 8,007,503 B2 | 8/2011 | Catanese et al. |
| 8,043,309 B2 | 10/2011 | Catanese et al. |
| 8,114,070 B2 | 2/2012 | Rubinsky et al. |
| 8,145,321 B2 | 3/2012 | Gross |
| 8,152,804 B2 | 4/2012 | Elmouelhi et al. |
| 8,157,815 B2 | 4/2012 | Catanese et al. |
| 8,162,960 B2 | 4/2012 | Manzo |

(56) References Cited

U.S. PATENT DOCUMENTS

| | | |
|---|---|---|
| 8,167,830 B2 | 5/2012 | Noriega |
| 8,211,118 B2 | 7/2012 | Catanese et al. |
| 8,216,254 B2 | 7/2012 | McLean et al. |
| 8,236,011 B2 | 8/2012 | Harris et al. |
| 8,251,985 B2 | 8/2012 | Hoey et al. |
| 8,273,079 B2 | 9/2012 | Hoey et al. |
| 8,298,132 B2 | 10/2012 | Connors et al. |
| 8,303,604 B2 | 11/2012 | Stone et al. |
| 8,308,765 B2 | 11/2012 | Saadat et al. |
| 8,333,776 B2 | 12/2012 | Cheng et al. |
| 8,343,187 B2 | 1/2013 | Lamson et al. |
| 8,361,112 B2 | 1/2013 | Kempton et al. |
| 8,372,065 B2 | 2/2013 | Hoey et al. |
| 8,388,611 B2 | 3/2013 | Shadduck et al. |
| 8,388,653 B2 | 3/2013 | Nobis et al. |
| 8,394,110 B2 | 3/2013 | Catanese et al. |
| 8,394,113 B2 | 3/2013 | Wei et al. |
| 8,419,723 B2 | 4/2013 | Shadduck et al. |
| 8,425,535 B2 | 4/2013 | McLean et al. |
| 8,444,657 B2 | 5/2013 | Saadat et al. |
| 8,454,655 B2 | 6/2013 | Yeung et al. |
| 8,465,551 B1 | 6/2013 | Wijay et al. |
| 8,480,686 B2 | 7/2013 | Bakos et al. |
| 8,491,606 B2 | 7/2013 | Tong et al. |
| 8,496,684 B2 | 7/2013 | Crainich et al. |
| 8,521,257 B2 | 8/2013 | Whitcomb et al. |
| 8,529,584 B2 | 9/2013 | Catanese et al. |
| 8,529,588 B2 | 9/2013 | Ahlberg et al. |
| 8,562,646 B2 | 10/2013 | Gellman et al. |
| 8,585,692 B2 | 11/2013 | Shadduck et al. |
| 8,603,106 B2 | 12/2013 | Catanese et al. |
| 8,603,123 B2 | 12/2013 | Todd |
| 8,603,187 B2 | 12/2013 | Kilemnick et al. |
| 8,628,542 B2 | 1/2014 | Merrick et al. |
| 8,663,243 B2 | 3/2014 | Lamson et al. |
| 8,668,705 B2 | 3/2014 | Johnston et al. |
| 8,683,895 B2 | 4/2014 | Nash |
| 8,715,239 B2 | 5/2014 | Lamson et al. |
| 8,715,298 B2 | 5/2014 | Catanese et al. |
| 8,734,469 B2 | 5/2014 | Pribanic et al. |
| 8,790,356 B2 | 7/2014 | Darois et al. |
| 8,801,702 B2 | 8/2014 | Hoey et al. |
| 8,808,363 B2 | 8/2014 | Perry et al. |
| 8,814,856 B2 | 8/2014 | Elmouelhi et al. |
| 8,828,035 B2 | 9/2014 | Kim |
| 8,834,458 B2 | 9/2014 | Neuberger et al. |
| 8,880,195 B2 | 11/2014 | Azure |
| 8,900,293 B2 | 12/2014 | Forbes et al. |
| 8,920,437 B2 | 12/2014 | Harris et al. |
| 8,926,494 B1 | 1/2015 | Cook et al. |
| 8,945,114 B2 | 2/2015 | Elmouelhi et al. |
| 9,034,001 B2 | 5/2015 | Cheng et al. |
| 9,039,740 B2 | 5/2015 | Wales et al. |
| 9,089,320 B2 | 7/2015 | Spivey et al. |
| 9,150,817 B2 | 10/2015 | Furihata et al. |
| 9,179,991 B2 | 11/2015 | Gozzi et al. |
| 9,204,922 B2 | 12/2015 | Hooven |
| 9,211,155 B2 | 12/2015 | Fruland et al. |
| 9,220,874 B2 | 12/2015 | Pillai et al. |
| 9,272,140 B2 | 3/2016 | Gerber |
| 9,277,914 B2 | 3/2016 | Wales et al. |
| 9,345,507 B2 | 5/2016 | Hoey et al. |
| 9,345,867 B2 | 5/2016 | Browning |
| 9,393,007 B2 | 7/2016 | Darois et al. |
| 9,439,643 B2 | 9/2016 | Darois et al. |
| 9,459,751 B2 | 10/2016 | Weaver et al. |
| 9,526,555 B2 | 12/2016 | Hoey et al. |
| 9,549,739 B2 | 1/2017 | Catanese et al. |
| 9,561,025 B2 | 2/2017 | Stone et al. |
| 9,592,044 B2 | 3/2017 | Weir et al. |
| 9,597,145 B2 | 3/2017 | Nelson et al. |
| 9,668,803 B2 | 6/2017 | Bhushan et al. |
| 9,675,373 B2 | 6/2017 | Todd |
| 9,750,492 B2 | 9/2017 | Ziniti et al. |
| 9,931,192 B2 | 4/2018 | McLean et al. |
| 10,130,353 B2 | 11/2018 | Catanese et al. |
| 10,702,261 B2 | 7/2020 | Stiggelbout |
| 11,331,093 B2 | 5/2022 | Catanese et al. |
| 11,471,148 B2 | 10/2022 | Lamson et al. |
| 11,504,149 B2 | 11/2022 | Merrick et al. |
| 11,672,520 B2 | 6/2023 | Lamson et al. |
| 11,850,140 B2 | 12/2023 | Lamson et al. |
| 2001/0041916 A1 | 11/2001 | Bonutti |
| 2001/0044639 A1 | 11/2001 | Levinson |
| 2002/0049453 A1 | 4/2002 | Nobles et al. |
| 2002/0095064 A1 | 7/2002 | Beyar |
| 2002/0095154 A1 | 7/2002 | Atkinson et al. |
| 2002/0107540 A1 | 8/2002 | Whalen et al. |
| 2002/0128684 A1 | 9/2002 | Foerster |
| 2002/0161382 A1 | 10/2002 | Neisz et al. |
| 2002/0177866 A1 | 11/2002 | Weikel et al. |
| 2002/0183740 A1 | 12/2002 | Edwards et al. |
| 2002/0193809 A1 | 12/2002 | Meade et al. |
| 2003/0023248 A1 | 1/2003 | Parodi |
| 2003/0040803 A1 | 2/2003 | Rioux et al. |
| 2003/0060819 A1 | 3/2003 | McGovern et al. |
| 2003/0078601 A1 | 4/2003 | Shikhman et al. |
| 2003/0109769 A1 | 6/2003 | Lowery et al. |
| 2003/0120309 A1 | 6/2003 | Colleran et al. |
| 2003/0130575 A1 | 7/2003 | Desai |
| 2003/0144570 A1 | 7/2003 | Hunter et al. |
| 2003/0176883 A1 | 9/2003 | Sauer et al. |
| 2003/0191497 A1 | 10/2003 | Cope |
| 2003/0199860 A1 | 10/2003 | Loeb et al. |
| 2003/0204195 A1 | 10/2003 | Keane et al. |
| 2003/0229263 A1 | 12/2003 | Connors et al. |
| 2003/0236535 A1 | 12/2003 | Onuki et al. |
| 2004/0010301 A1 | 1/2004 | Kindlein et al. |
| 2004/0030217 A1 | 2/2004 | Yeung et al. |
| 2004/0043052 A1 | 3/2004 | Hunter et al. |
| 2004/0044350 A1 | 3/2004 | Martin et al. |
| 2004/0078046 A1 | 4/2004 | Barzell et al. |
| 2004/0092978 A1 | 5/2004 | Surti |
| 2004/0122456 A1 | 6/2004 | Saadat et al. |
| 2004/0122474 A1 | 6/2004 | Gellman et al. |
| 2004/0143343 A1 | 7/2004 | Grocela |
| 2004/0147958 A1 | 7/2004 | Lam et al. |
| 2004/0162568 A1 | 8/2004 | Saadat et al. |
| 2004/0167635 A1 | 8/2004 | Yachia et al. |
| 2004/0172046 A1 | 9/2004 | Hlavka et al. |
| 2004/0181235 A1 | 9/2004 | Daignault et al. |
| 2004/0193191 A1 | 9/2004 | Starksen et al. |
| 2004/0193194 A1 | 9/2004 | Laufer et al. |
| 2004/0193196 A1 | 9/2004 | Appling et al. |
| 2004/0194790 A1 | 10/2004 | Laufer et al. |
| 2004/0215179 A1 | 10/2004 | Swoyer et al. |
| 2004/0215181 A1 | 10/2004 | Christopherson et al. |
| 2004/0230316 A1 | 11/2004 | Cioanta et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0010203 A1 | 1/2005 | Edwards et al. |
| 2005/0013805 A1 | 1/2005 | Tavori |
| 2005/0033403 A1 | 2/2005 | Ward et al. |
| 2005/0055087 A1 | 3/2005 | Starksen |
| 2005/0059929 A1 | 3/2005 | Bolmsjo et al. |
| 2005/0065550 A1 | 3/2005 | Starksen et al. |
| 2005/0080454 A1 | 4/2005 | Drews et al. |
| 2005/0101982 A1 | 5/2005 | Ravenscroft et al. |
| 2005/0107811 A1 | 5/2005 | Starksen et al. |
| 2005/0107812 A1 | 5/2005 | Starksen et al. |
| 2005/0137716 A1 | 6/2005 | Gross |
| 2005/0154401 A1 | 7/2005 | Weldon et al. |
| 2005/0165272 A1 | 7/2005 | Okada et al. |
| 2005/0171522 A1 | 8/2005 | Christopherson |
| 2005/0177181 A1 | 8/2005 | Kagan et al. |
| 2005/0192652 A1 | 9/2005 | Cioanta et al. |
| 2005/0203344 A1 | 9/2005 | Orban et al. |
| 2005/0203550 A1 | 9/2005 | Laufer et al. |
| 2005/0216040 A1 | 9/2005 | Gertner et al. |
| 2005/0216078 A1 | 9/2005 | Starksen et al. |
| 2005/0222557 A1 | 10/2005 | Baxter et al. |

(56) References Cited

U.S. PATENT DOCUMENTS

| | | |
|---|---|---|
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251206 A1 | 11/2005 | Maahs et al. |
| 2005/0256530 A1 | 11/2005 | Petros |
| 2005/0267405 A1 | 12/2005 | Shah |
| 2005/0273138 A1 | 12/2005 | To et al. |
| 2005/0283189 A1 | 12/2005 | Rosenblatt |
| 2005/0288694 A1 | 12/2005 | Solomon |
| 2006/0004410 A1 | 1/2006 | Nobis et al. |
| 2006/0020276 A1 | 1/2006 | Saadat et al. |
| 2006/0020327 A1 | 1/2006 | Lashinski et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0026750 A1 | 2/2006 | Ballance |
| 2006/0030884 A1 | 2/2006 | Yeung et al. |
| 2006/0058817 A1 | 3/2006 | Starksen et al. |
| 2006/0079880 A1 | 4/2006 | Sage et al. |
| 2006/0079881 A1 | 4/2006 | Christopherson et al. |
| 2006/0089636 A1 | 4/2006 | Christopherson et al. |
| 2006/0089646 A1 | 4/2006 | Bonutti |
| 2006/0095058 A1 | 5/2006 | Sivan et al. |
| 2006/0155308 A1 | 7/2006 | Griego |
| 2006/0167477 A1 | 7/2006 | Arcia et al. |
| 2006/0167533 A1 | 7/2006 | Spraker et al. |
| 2006/0178680 A1 | 8/2006 | Nelson et al. |
| 2006/0189940 A1 | 8/2006 | Kirsch |
| 2006/0195008 A1 | 8/2006 | Whalen et al. |
| 2006/0199996 A1 | 9/2006 | Caraballo et al. |
| 2006/0241694 A1 | 10/2006 | Cerundolo |
| 2006/0265042 A1 | 11/2006 | Catanese et al. |
| 2006/0271032 A1 | 11/2006 | Chin et al. |
| 2006/0276481 A1 | 12/2006 | Evrard et al. |
| 2006/0276871 A1* | 12/2006 | Lamson .............. A61B 17/42 623/1.11 |
| 2006/0282081 A1 | 12/2006 | Fanton et al. |
| 2007/0049929 A1 | 3/2007 | Catanese et al. |
| 2007/0049970 A1 | 3/2007 | Belef et al. |
| 2007/0060931 A1 | 3/2007 | Hamilton et al. |
| 2007/0073322 A1 | 3/2007 | Mikkaichi et al. |
| 2007/0073342 A1 | 3/2007 | Stone et al. |
| 2007/0088362 A1 | 4/2007 | Bonutti et al. |
| 2007/0100421 A1 | 5/2007 | Griffin |
| 2007/0112385 A1 | 5/2007 | Conlon |
| 2007/0142846 A1 | 6/2007 | Catanese et al. |
| 2007/0173888 A1 | 7/2007 | Gertner et al. |
| 2007/0179491 A1 | 8/2007 | Kratoska et al. |
| 2007/0179496 A1 | 8/2007 | Swoyer et al. |
| 2007/0198038 A1 | 8/2007 | Cohen et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0021485 A1 | 1/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039893 A1 | 2/2008 | McLean et al. |
| 2008/0039894 A1 | 2/2008 | Catanese et al. |
| 2008/0039921 A1 | 2/2008 | Wallsten et al. |
| 2008/0045978 A1 | 2/2008 | Kuhns et al. |
| 2008/0051810 A1 | 2/2008 | To et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0161852 A1 | 7/2008 | Kaiser et al. |
| 2008/0195145 A1 | 8/2008 | Bonutti et al. |
| 2008/0208220 A1 | 8/2008 | Shiono et al. |
| 2008/0221388 A1 | 9/2008 | Seibel et al. |
| 2008/0228202 A1 | 9/2008 | Cropper et al. |
| 2008/0262424 A1 | 10/2008 | Hooft |
| 2008/0269737 A1 | 10/2008 | Elmouelhi et al. |
| 2009/0012537 A1 | 1/2009 | Green |
| 2009/0018553 A1 | 1/2009 | McLean et al. |
| 2009/0060977 A1 | 3/2009 | Lamson et al. |
| 2009/0112234 A1 | 4/2009 | Crainich et al. |
| 2009/0112537 A1 | 4/2009 | Okumura |
| 2009/0118762 A1 | 5/2009 | Crainch et al. |
| 2009/0163934 A1 | 6/2009 | Raschdorf, Jr. et al. |
| 2009/0177288 A1 | 7/2009 | Wallsten |
| 2009/0198227 A1 | 8/2009 | Prakash |
| 2009/0204128 A1 | 8/2009 | Lamson et al. |
| 2010/0010631 A1 | 1/2010 | Otte et al. |
| 2010/0023022 A1 | 1/2010 | Zeiner et al. |
| 2010/0023024 A1 | 1/2010 | Zeiner et al. |
| 2010/0023025 A1 | 1/2010 | Zeiner et al. |
| 2010/0023026 A1 | 1/2010 | Zeiner et al. |
| 2010/0030262 A1 | 2/2010 | McLean et al. |
| 2010/0030263 A1 | 2/2010 | Cheng et al. |
| 2010/0049188 A1 | 2/2010 | Nelson et al. |
| 2010/0063351 A1 | 3/2010 | Witzmann et al. |
| 2010/0063542 A1 | 3/2010 | Burg et al. |
| 2010/0114162 A1 | 5/2010 | Bojarski et al. |
| 2010/0130815 A1 | 5/2010 | Gross et al. |
| 2010/0191045 A1 | 7/2010 | Gobron et al. |
| 2010/0256442 A1 | 10/2010 | Ogdahl et al. |
| 2010/0261950 A1 | 10/2010 | Lund et al. |
| 2010/0286106 A1 | 11/2010 | Gat et al. |
| 2010/0286679 A1 | 11/2010 | Hoey et al. |
| 2010/0286717 A1 | 11/2010 | Heinrich et al. |
| 2010/0298948 A1 | 11/2010 | Hoey et al. |
| 2010/0324669 A1 | 12/2010 | Hlavka et al. |
| 2011/0040312 A1 | 2/2011 | Lamson et al. |
| 2011/0046648 A1 | 2/2011 | Johnston et al. |
| 2011/0060349 A1 | 3/2011 | Cheng et al. |
| 2011/0077676 A1 | 3/2011 | Sivan et al. |
| 2011/0082471 A1 | 4/2011 | Holcomb et al. |
| 2011/0105841 A1 | 5/2011 | Kutikov et al. |
| 2011/0144423 A1 | 6/2011 | Tong et al. |
| 2011/0152839 A1 | 6/2011 | Cima et al. |
| 2011/0160747 A1 | 6/2011 | McLean et al. |
| 2011/0166564 A1 | 7/2011 | Merrick et al. |
| 2011/0172755 A1 | 7/2011 | Nelson et al. |
| 2011/0190758 A1 | 8/2011 | Lamson et al. |
| 2011/0196393 A1 | 8/2011 | Eliachar et al. |
| 2011/0202052 A1 | 8/2011 | Gelbart et al. |
| 2011/0218387 A1 | 9/2011 | Lamson et al. |
| 2011/0245828 A1 | 10/2011 | Baxter et al. |
| 2011/0276081 A1 | 11/2011 | Kilemnik |
| 2011/0276086 A1 | 11/2011 | Al-Qbandi et al. |
| 2012/0010645 A1 | 1/2012 | Feld |
| 2012/0041533 A1 | 2/2012 | Bertolino et al. |
| 2012/0041534 A1 | 2/2012 | Clerc et al. |
| 2012/0059387 A1 | 3/2012 | Schanz et al. |
| 2012/0165837 A1 | 6/2012 | Belman et al. |
| 2012/0203250 A1 | 8/2012 | Weir et al. |
| 2012/0245600 A1 | 9/2012 | McLean et al. |
| 2012/0265006 A1 | 10/2012 | Makower et al. |
| 2013/0096582 A1 | 4/2013 | Cheng et al. |
| 2013/0178871 A1 | 7/2013 | Koogle et al. |
| 2013/0197547 A1 | 8/2013 | Fukuoka et al. |
| 2013/0211431 A1 | 8/2013 | Wei et al. |
| 2013/0253574 A1 | 9/2013 | Catanese et al. |
| 2013/0253662 A1 | 9/2013 | Lamson et al. |
| 2013/0261383 A1 | 10/2013 | Catanese et al. |
| 2013/0261665 A1 | 10/2013 | Yeung et al. |
| 2013/0267772 A1 | 10/2013 | Catanese et al. |
| 2013/0268001 A1 | 10/2013 | Catanese et al. |
| 2013/0274799 A1 | 10/2013 | Catanese et al. |
| 2013/0289342 A1 | 10/2013 | Tong et al. |
| 2013/0296639 A1 | 11/2013 | Lamson et al. |
| 2013/0296889 A1 | 11/2013 | Tong et al. |
| 2013/0296935 A1 | 11/2013 | McLean et al. |
| 2013/0325143 A1 | 12/2013 | Lamson et al. |
| 2014/0005473 A1 | 1/2014 | Catanese et al. |

(56) References Cited

U.S. PATENT DOCUMENTS

| | | |
|---|---|---|
| 2014/0005690 A1 | 1/2014 | Catanese et al. |
| 2014/0012192 A1 | 1/2014 | Bar-On et al. |
| 2014/0031835 A1 | 1/2014 | Viker et al. |
| 2014/0088587 A1 | 3/2014 | Merrick et al. |
| 2014/0180067 A1 | 6/2014 | Stigall et al. |
| 2014/0207179 A1 | 7/2014 | Farhangnia et al. |
| 2014/0221981 A1 | 8/2014 | Cima et al. |
| 2014/0236230 A1 | 8/2014 | Johnston et al. |
| 2014/0275756 A1 | 9/2014 | Bender et al. |
| 2014/0288637 A1 | 9/2014 | Clerc et al. |
| 2014/0296881 A1 | 10/2014 | Ranucci et al. |
| 2015/0025652 A1 | 1/2015 | McLean et al. |
| 2015/0112299 A1 | 4/2015 | Forbes et al. |
| 2015/0127050 A1 | 5/2015 | Lamson et al. |
| 2015/0157309 A1 | 6/2015 | Bird |
| 2015/0257908 A1 | 9/2015 | Chao et al. |
| 2015/0335393 A1 | 11/2015 | Ciulla et al. |
| 2015/0351743 A1 | 12/2015 | Stiggelbout |
| 2016/0000455 A1 | 1/2016 | Golan et al. |
| 2016/0022265 A1 | 1/2016 | Kawaura et al. |
| 2016/0038087 A1 | 2/2016 | Hunter |
| 2016/0045297 A1 | 2/2016 | Siegel et al. |
| 2016/0051735 A1 | 2/2016 | Slepian |
| 2016/0081736 A1 | 3/2016 | Hoey et al. |
| 2016/0089140 A1 | 3/2016 | Kawaura et al. |
| 2016/0095685 A1 | 4/2016 | Vemuri et al. |
| 2016/0096009 A1 | 4/2016 | Feld |
| 2016/0120647 A1 | 5/2016 | Rogers et al. |
| 2016/0206370 A1 | 7/2016 | Fruland et al. |
| 2016/0242894 A1 | 8/2016 | Davis |
| 2016/0302904 A1 | 10/2016 | Ogdahl et al. |
| 2016/0317180 A1 | 11/2016 | Kilemnik |
| 2017/0000598 A1 | 1/2017 | Bachar |
| 2017/0128741 A1 | 5/2017 | Keltner et al. |
| 2017/0135830 A1 | 5/2017 | Harkin et al. |
| 2017/0156723 A1 | 6/2017 | Keating et al. |
| 2018/0103945 A1 | 4/2018 | Ciulla et al. |
| 2018/0146964 A1 | 5/2018 | Garcia et al. |
| 2018/0318114 A1 | 11/2018 | Huang et al. |
| 2018/0353181 A1 | 12/2018 | Wei |
| 2019/0125334 A1 | 5/2019 | Tong et al. |
| 2020/0022692 A1 | 1/2020 | Lamson et al. |
| 2020/0038213 A1 | 2/2020 | Bly et al. |
| 2020/0121442 A1 | 4/2020 | Askeland |
| 2021/0145619 A1 | 5/2021 | Bly et al. |
| 2021/0161641 A1 | 6/2021 | Bachar |
| 2021/0161642 A1 | 6/2021 | Jen et al. |
| 2021/0307641 A1 | 10/2021 | Rumbles et al. |
| 2021/0378784 A1 | 12/2021 | Welch et al. |
| 2022/0000445 A1 | 1/2022 | Datta et al. |
| 2022/0031357 A1 | 2/2022 | Cutts et al. |
| 2022/0031358 A1 | 2/2022 | Yarra et al. |
| 2022/0031389 A1 | 2/2022 | Fischell et al. |
| 2022/0061834 A1 | 3/2022 | Chung et al. |
| 2022/0125499 A1 | 4/2022 | Hoey et al. |
| 2022/0133462 A1 | 5/2022 | Kilemnik |
| 2022/0142464 A1 | 5/2022 | Petroff et al. |
| 2022/0240925 A1 | 8/2022 | Epstein et al. |
| 2022/0249219 A1 | 8/2022 | Chung et al. |
| 2022/0265262 A1 | 8/2022 | Melsheimer |
| 2022/0273918 A1 | 9/2022 | Ghriallais et al. |
| 2022/0378577 A1 | 12/2022 | Anderson et al. |
| 2022/0395363 A1 | 12/2022 | Ghriallais et al. |
| 2023/0022482 A1 | 1/2023 | Dhavale |
| 2023/0200802 A1 | 6/2023 | Catanese, III |
| 2023/0225720 A1 | 7/2023 | Lamson et al. |
| 2023/0225851 A1 | 7/2023 | Lamson et al. |
| 2023/0293166 A1 | 9/2023 | Lamson et al. |

FOREIGN PATENT DOCUMENTS

| | | |
|---|---|---|
| CN | 101795641 A | 8/2010 |
| CN | 102112064 B | 6/2014 |
| CN | 105852938 A | 8/2016 |
| CN | 105919695 A | 9/2016 |
| CN | 109675177 A | 4/2019 |
| CN | 211156119 U | 8/2020 |
| CN | 112891032 A | 6/2021 |
| CN | 216221843 U | 4/2022 |
| DE | 10159470 A1 | 6/2003 |
| DE | 102019101987 A1 | 7/2020 |
| EP | 0246836 B1 | 12/1991 |
| EP | 0464480 A1 | 1/1992 |
| EP | 0274846 B1 | 2/1994 |
| EP | 0632999 A1 | 1/1995 |
| EP | 0667126 A1 | 8/1995 |
| EP | 1016377 A2 | 7/2000 |
| EP | 1482841 A1 | 12/2004 |
| EP | 1082941 B1 | 3/2005 |
| EP | 1006909 B1 | 1/2007 |
| EP | 1852071 A2 | 11/2007 |
| EP | 1584295 B1 | 2/2008 |
| EP | 1884198 A2 | 2/2008 |
| EP | 1884199 A1 | 2/2008 |
| EP | 1670361 B1 | 4/2008 |
| EP | 1331886 B1 | 12/2008 |
| EP | 1482840 B1 | 12/2008 |
| EP | 2243507 A1 | 10/2010 |
| EP | 1484023 B1 | 5/2011 |
| EP | 2345373 A1 | 7/2011 |
| EP | 2345374 A1 | 7/2011 |
| EP | 2049023 B1 | 12/2014 |
| EP | 3167845 A1 | 5/2017 |
| FR | 2750031 A1 | 12/1997 |
| JP | 5836559 A | 3/1983 |
| JP | 09122134 | 5/1997 |
| JP | 3370300 B2 | 1/2003 |
| JP | 2004344427 A | 12/2004 |
| JP | 2009521278 A | 6/2009 |
| JP | 2011529745 A | 12/2011 |
| JP | 2012143622 A | 8/2012 |
| JP | 2023502729 A | 1/2023 |
| KR | 20060009698 A | 2/2006 |
| KR | 101534820 B1 | 7/2015 |
| RU | 2062121 C1 | 6/1996 |
| RU | 2112571 C1 | 6/1998 |
| RU | 2128012 C1 | 3/1999 |
| RU | 2221501 C2 | 1/2004 |
| SU | 825094 A1 | 4/1981 |
| WO | 1987001270 A1 | 3/1987 |
| WO | 1992010142 A1 | 6/1992 |
| WO | 1993004727 A1 | 3/1993 |
| WO | 1993015664 A1 | 8/1993 |
| WO | 1994026170 A1 | 11/1994 |
| WO | 1995000818 A1 | 1/1995 |
| WO | 2000040159 A1 | 7/2000 |
| WO | 2001026588 A2 | 4/2001 |
| WO | 2001028432 A1 | 4/2001 |
| WO | 2001039671 A1 | 6/2001 |
| WO | 2001049195 A1 | 7/2001 |
| WO | 2001095818 A1 | 12/2001 |
| WO | 2002028289 A1 | 4/2002 |
| WO | 2002030335 A2 | 4/2002 |
| WO | 2002032321 A1 | 4/2002 |
| WO | 2002058577 A1 | 8/2002 |
| WO | 2003039334 A2 | 5/2003 |
| WO | 2003077772 A1 | 9/2003 |
| WO | 2004000159 A2 | 12/2003 |
| WO | 2004017845 A1 | 3/2004 |
| WO | 2004019787 A2 | 3/2004 |
| WO | 2004019788 A2 | 3/2004 |
| WO | 2004030569 A2 | 4/2004 |
| WO | 2004066875 A1 | 8/2004 |
| WO | 2004080529 A2 | 9/2004 |
| WO | 2004103189 A1 | 12/2004 |
| WO | 2005034738 A2 | 4/2005 |
| WO | 2005065412 A2 | 7/2005 |
| WO | 2005094447 A2 | 10/2005 |
| WO | 2006127241 A2 | 11/2006 |
| WO | 2006127431 A2 | 11/2006 |
| WO | 2007048437 A1 | 5/2007 |
| WO | 2007053516 A2 | 5/2007 |
| WO | 2007064906 A2 | 6/2007 |
| WO | 2007075981 A2 | 7/2007 |

(56) References Cited

FOREIGN PATENT DOCUMENTS

| WO | 2008002340 | A2 | 1/2008 |
|---|---|---|---|
| WO | 2008006084 | A2 | 1/2008 |
| WO | 2008014191 | A2 | 1/2008 |
| WO | 2008043044 | A2 | 4/2008 |
| WO | 2008043917 | A2 | 4/2008 |
| WO | 2008097942 | A1 | 8/2008 |
| WO | 2008132735 | A1 | 11/2008 |
| WO | 2008142677 | A2 | 11/2008 |
| WO | 2009009617 | A1 | 1/2009 |
| WO | 2009072131 | A2 | 6/2009 |
| WO | 2010011832 | A1 | 1/2010 |
| WO | 2010014821 | A2 | 2/2010 |
| WO | 2010014825 | A1 | 2/2010 |
| WO | 2010065214 | A2 | 6/2010 |
| WO | 2010086849 | A1 | 8/2010 |
| WO | 2010106543 | A2 | 9/2010 |
| WO | 2011084712 | A1 | 7/2011 |
| WO | 2012018446 | A2 | 2/2012 |
| WO | 2012028843 | A1 | 3/2012 |
| WO | 2012079548 | A1 | 6/2012 |
| WO | 2012079549 | A2 | 6/2012 |
| WO | 2012091952 | A2 | 7/2012 |
| WO | 2012091954 | A2 | 7/2012 |
| WO | 2012091955 | A2 | 7/2012 |
| WO | 2012091956 | A2 | 7/2012 |
| WO | 2012123950 | A2 | 9/2012 |
| WO | 2014003987 | A1 | 1/2014 |
| WO | 2014035506 | A2 | 3/2014 |
| WO | 2014145381 | A1 | 9/2014 |
| WO | 2014153219 | A1 | 9/2014 |
| WO | 2014200764 | A1 | 12/2014 |
| WO | 2015101975 | A1 | 7/2015 |
| WO | 2016134166 | A1 | 8/2016 |
| WO | 2017017499 | A1 | 2/2017 |
| WO | 2017081326 | A2 | 5/2017 |
| WO | 2017112856 | A1 | 6/2017 |
| WO | 2021190092 | A1 | 9/2021 |

OTHER PUBLICATIONS

Response to Office Action filed Sep. 8, 2023, in co-pending U.S. Appl. No. 18/181,797.
European Extended Search Report and Search Opinion mailed Jun. 16, 2023, in EP Application No. 23169061.1.
Office Action mailed Jun. 8, 2023, in co-pending U.S. Appl. No. 18/181,797.
U.S. Appl. No. 16/166,312, filed Oct. 22, 2018.
Bacharova, O.A., et al. "The Effect of Rhodiolae rosea Extract on Incidence Rate of Superficial Bladder Carcinoma Relapses", Kozin 1995.
Berges, Richard, et al. "Alternative Minimalinvasive Therapien Beim Benignen Prostatasyndrom", Medizin, Jg. 104, Heft 37, Sep. 14, 2007.
Borzhievski, et al., "Tactics of the Surgical Treatment of Patients With Prostatic Adenoma and Acute Urinary Retention," Urologia Nefrol (Mosk), Jan.-Feb. 1987, (1):39-43.
European Search Report for EP Application No. 06770621.8, mailed Sep. 20, 2012.
European Search Report for EP Application No. 06845991.6, mailed on Mar. 22, 2013.
European Search Report for EP Application No. 07840462.1, mailed May 29, 2012.
European Search Report for EP Application No. 08729001.1, mailed on Feb. 4, 2014.
European Search Report for EP Application No. 08772483.7, mailed on Feb. 12, 2015.
European Search Report for EP Application No. 11154962.2, mailed on May 19, 2011.
European Search Report for EP Application No. 11154976.2, mailed on Jun. 6, 2011.
European Search Report for EP Application No. 11814950.9, mailed on Sept. 8, 2015.
European Search Report for EP Application No. 11852778.7, mailed on Nov. 19, 2015.
European Search Report for EP Application No. 11854148.1, mailed on Oct. 20, 2017.
European Search Report for EP Application No. 13810314.8, mailed on Apr. 6, 2016.
European Search Report for EP Application No. 17150545.6, mailed on Sep. 11, 2017.
Hartung, Rudolf, et al. "Instrumentelle Therapie der benignen Prostatahyperplasie", Medizin, Deutsches Arzteblatt 97, Heft 15, Apr. 14, 2000.
Hofner, Klaus, et al., "Operative Therapie des benignen Prostatasyndroms", Medizin, Dtsch Arztebl, 2007; 104(36): A 2424-9.
Hubmann, R. "Geschichte der transurethralen Prostataeingriffe", Geschichte der Medizin, Urologe [B], 2000, 40:152-160.
International Search Report for PCT Application No. PCT/US2006/019372, mailed on May 2, 2008.
International Search Report for PCT Application No. PCT/US2006/048962, mailed Dec. 10, 2008.
International Search Report for PCT Application No. PCT/US2007/074019, mailed on Jul. 25, 2008.
International Search Report for PCT Application No. PCT/US2008/053001, mailed on Jun. 17, 2008.
International Search Report for PCT Application No. PCT/US2008/069560, mailed on Sep. 8, 2008.
International Search Report for PCT Application No. PCT/US2009/052271, mailed on Apr. 7, 2010.
International Search Report for PCT Application No. PCT/US2009/052275, mailed on Oct. 9, 2009.
International Search Report for PCT Application No. PCT/US2011/041200, mailed on Feb. 17, 2012.
International Search Report for PCT Application No. PCT/US2011/065348, mailed on Jun. 21, 2012.
International Search Report for PCT Application No. PCT/US2011/065358, mailed on Jun. 21, 2012.
International Search Report for PCT Application No. PCT/US2011/065377, mailed on Aug. 29, 2012.
International Search Report for PCT Application No. PCT/US2011/065386, mailed on Jun. 28, 2012.
International Search Report for PCT Application No. PCT/US2013/044035, mailed on Sept. 6, 2013.
Jonas, U., et al., "Benigne Prostatahyperplasie", Der Urologe 2006—[Sonderheft] 45:134-144.
Kruck, S., et al., "Aktuelle Therapiemoglichkeiten des Benignen Prostata-Syndroms", J Urol Urogynakol, 2009; 16(1): 19-22.
Miyake, Osamu. "Medical Examination and Treatment for BPH," Pharma Med, vol. 22, No. 3, 2004, p. 97-103.
Reich, O., et al., "Benignes Prostatasyndrom (BPS)," Der Urologe A Issue vol. 45, No. 6, Jun. 2006, p. 769-782.
Schauer, P., et al. "New applications for endoscopy: the emerging field of endoluminal and transgastric bariatric surgery", Surgical Endoscopy, (Apr. 24, 2006), 10 pgs.
Sharp, Howard T., M.D., et al. "Instruments and Methods—The 4-S Modification of the Roeder Knot: How to Tie It", Obstetrics & Gynecology, p. 1004-1006, vol. 90, No. 6, Dec. 1997.
Takashi, Daito. "Low-Invasive Treatment for BPH", Medico vol. 34, No. 10, p. 366-369, 2000.
Teruhisa, Ohashi. "Urinary Dysfunction by Lower Urinary Tract Obstruction in Male", Pharma Medica, vol. 8, No. 8, p. 35-39, 1990.
Tomohiko, Koyanagi, et al., "Surgery View of 21st Century," Urological Surgery, vol. 84, No. 1, p. 47-53, 2001.
Trapeznikov, et al., "New Technologies in the Treatment of Benign Prostatic Hyperplasia", Urologia Nefrol (Mosk), Jul.-Aug. 1996, (4):41-47.
Yeung, Jeff. "Treating Urinary Stress Incontenance Without Incision with Endoscopic Suture Anchor & Approximating Device," Aleeva Medical, Inc., 2007.
Office Action mailed Mar. 20, 2024, in co-pending U.S. Appl. No. 18/181,797.

(56) References Cited

OTHER PUBLICATIONS

Response to Office Action filed Nov. 20, 2023, in co-pending U.S. Appl. No. 18/181,797.
Extended European Search Report issued in Europe for European Patent Application No. 24193066.8, dated Dec. 17, 2024, 8 pgs.

\* cited by examiner

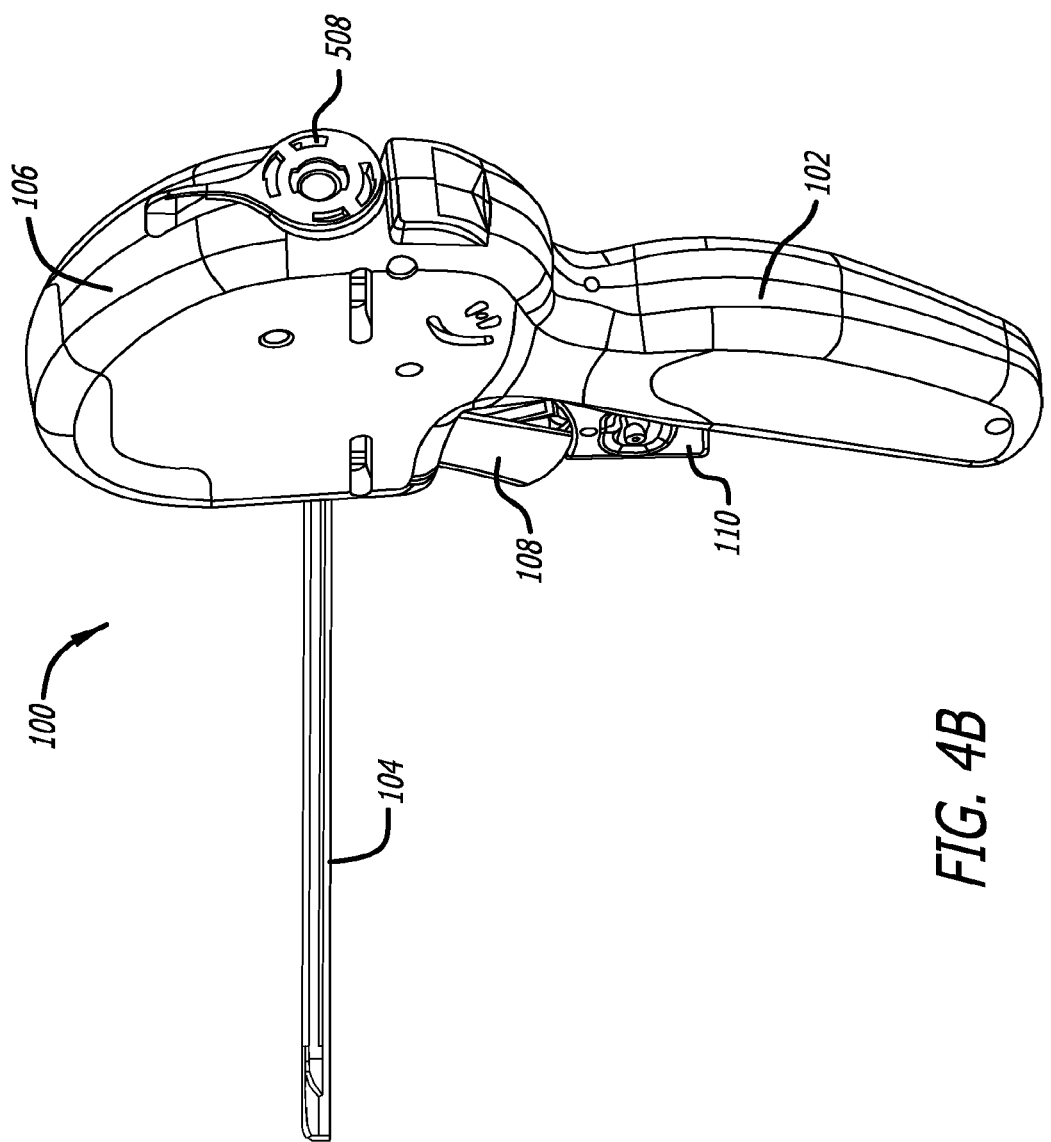

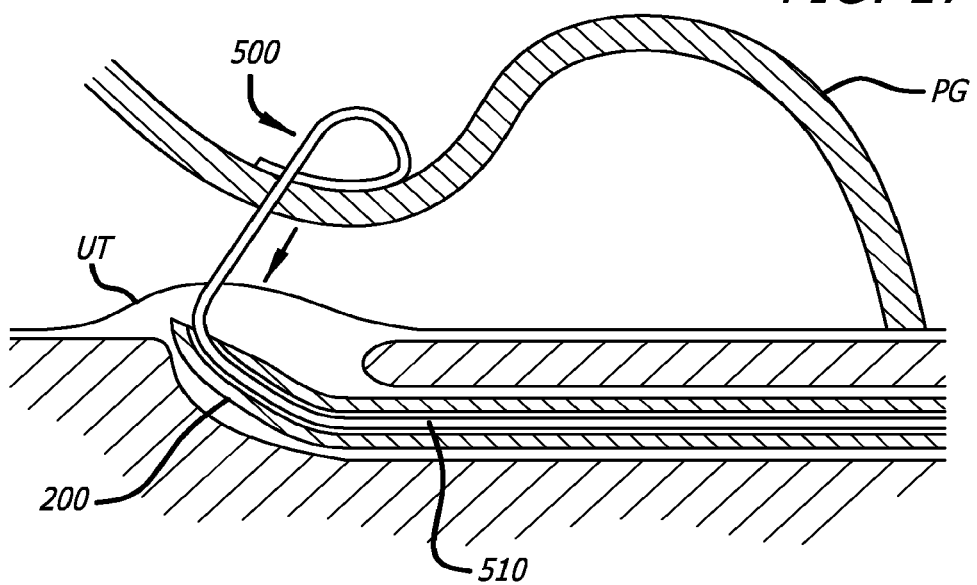
FIG. 17C
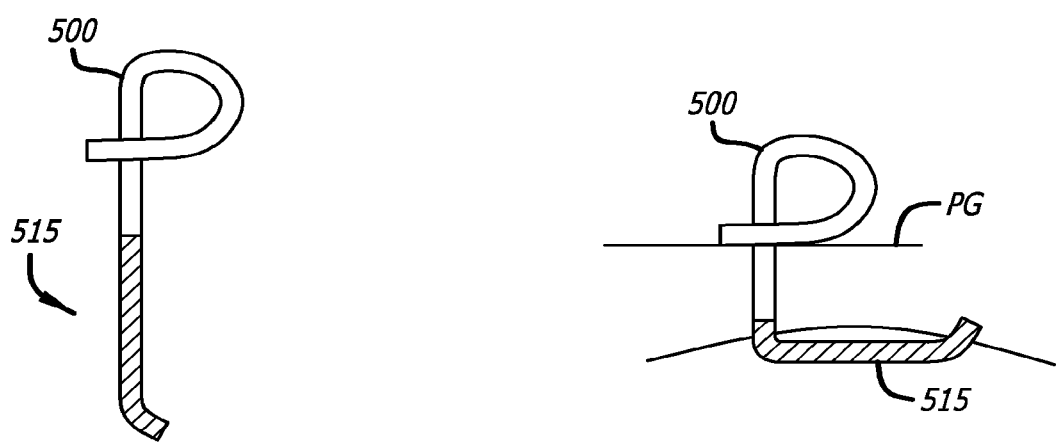
FIG. 18A
FIG. 18B

FLEXIBLE SYSTEM FOR DELIVERING AN ANCHOR

CROSS REFERENCE TO RELATED APPLICATIONS

This application is a continuation of U.S. patent application Ser. No. 16/166,312 filed Oct. 22, 2018, now issued as U.S. Pat. No. 11,331,093, which is a continuation of U.S. patent application Ser. No. 13/538,758 filed Jun. 29, 2012, now issued as U.S. Pat. No. 10,130,353, the entire disclosures of which are expressly incorporated herein by reference.

BACKGROUND OF THE DISCLOSURE

The present disclosure relates generally to medical devices and methods, and more particularly to systems and associated methods for manipulating or retracting tissues and anatomical or other structures within the body of human or animal subjects for the purpose of treating diseases or disorders.

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner end of the prostate gland to squeeze the urethra. This pressure on the urethra increases resistance to urine flow through the end of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry lower risks of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

There have been advances in developing minimally invasive devices and methods for lifting and repositioning of tissues. However, further advances are necessary to ensure an ability to access difficult to reach body structure.

There remains a need for the development of new devices and methods that can be used for various procedures where it is necessary to employ flexible or versatile devices for accessing target anatomy and minimizing patient discomfort. Changing the flexibility of interventional devices and maintaining positioning with respect to anatomy may additionally be necessary. In particular, there is a need for alternative apparatus and treatment approaches for the purpose of engaging or reaching anatomy from various angles. An ability to access anatomy with minimally invasive instruments while viewing the interventional procedure is also desirable. Moreover, various structures ensuring an effective interventional procedure such as implants having structural memory characteristics have been found to be helpful in certain treatment approaches.

The present disclosure addresses these and other needs.

SUMMARY

Briefly and in general terms, the present disclosure is directed towards an apparatus and method for deploying an anchor assembly within a patient's body to accomplish interventional treatments. A delivery device is provided to access the anatomy targeted for the interventional procedure. The delivery device includes flexible structure and a controllable position stability mechanism that can be configured to control one or more of axial deflection and longitudinal positioning.

The delivery apparatus of the present disclosure includes various subassemblies that are mobilized via an actuator or other manually accessible structure. The operation of the subassemblies is coordinated and synchronized to ensure accurate and precise implantation of an anchor assembly. In one embodiment, the delivery device is embodied in a tissue approximation assembly that is configured to treat BPH.

In one particular aspect, the present invention is directed towards a flexible delivery device that accomplishes the delivery of a first or distal anchor assembly component at a first location within a patient's body and the delivery of a second or proximal anchor assembly component at a second location within the patient. The flexible nature of an elongate portion of the delivery device is intended to minimize patient discomfort while providing structure to effectively reach an interventional site. In this regard, the delivery device can include a mechanism that accomplishes axial deflection of the elongate portion and/or a needle extending therefrom. The deflection mechanism can provide variable deflection of portions of the delivery device. The device can also accomplish imparting tension during delivery to a connector to hold it while attaching the proximal anchor in situ. The procedure can be viewed employing a scope inserted in the device. Also, the delivery device can be sized and shaped to be compatible inside a sheath up to 24 F, preferably a 19 F sheath or smaller.

The scope can assume various configurations and can be employed with complementary structure assisting in the viewing function. In one approach, a mirrored surface aids in viewing and in other approaches the scope includes a variable liquid filled lens or an annular lens.

The anchor assembly can be configured to accomplish approximating, retracting, lifting, compressing, supporting or repositioning tissue within the body of a human or animal subject. Moreover, the apparatus configured to deploy the anchor assembly as well as the anchor assembly itself are configured to complement and cooperate with body anatomy.

In one particular approach to a delivery device, an elongate member extends from a handle assembly. As an alternative to a rigid structure, the elongate member can assume flexible characteristics to minimize patient discomfort. In this way, the device can be advanced more easily within anatomy to a treatment site. The delivery device can further include a position maintaining or stability mechanism that holds the position of the flexible elongate member within anatomy.

To direct tissue penetrating structures such as a needle, the flexible elongate member can be equipped with a longitudinally transferrable wire that can be arranged to deflect a tip of the needle. The elongate member can alternatively embody segmented structure and a distal end portion that is expandable so that longitudinal positioning of the distal end of the member can be maintained in a desired configuration at an anatomical site. A multiple needle approach is also contemplated.

The implant itself can be placed within a sleeve or embody a tube sized to receive a wire. In this way, the implant can be delivered in a first configuration and then permitted to assume a second configuration upon deployment at a treatment site. Similar structure is also contemplated in connection with providing a temporary compression to tissue in respect of which an anchor assembly is subsequently placed.

Various alternative methods of use are contemplated. The disclosed apparatus can be used to improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has a myriad of other potential surgical, therapeutic, cosmetic or reconstructive applications, such as where a tissue, organ, graft or other material requires approximately, retracting, lifting, repositioning, compression or support.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIGS. 4A-C are side and perspective views, depicting one embodiment of a delivery device and various features thereof;

FIGS. 17A-C are side and partial cross-sectional views, depicting another approach to an implant and delivery system;

FIGS. 18A-B are side views, depicting yet another approach to an implant;

DETAILED DESCRIPTION OF THE PREFERRED EMBODIMENTS

Turning now to the figures, which are provided by way of example and not limitation, the present disclosure is directed to a flexible delivery device configured to deliver an anchor assembly within a patient's body for treatment purposes. The disclosed apparatus can be employed for various medical purposes including but not limited to retracting, lifting, compressing, approximating, supporting or repositioning tissues, organs, anatomical structures, grafts or other material found within a patient's body. Such tissue manipulation is intended to facilitate the treatment of diseases or disorders such as the displacement, compression and/or retraction of the body tissue.

In an aspect of the present disclosure, the delivery device includes a handle assembly supporting an elongate member having flexible characteristics. The elongate member defines a low profile that is suited to navigate body anatomy to reach an interventional site. Substructure is provided to maintain a longitudinal profile of the elongate member so that the interventional procedure can progress as intended. A controllable position stability mechanism is thus contemplated and the same can further maintain lateral positioning of the delivery device.

In another aspect, one portion of an anchor assembly or implant is positioned and implanted against a first section of anatomy. A second portion of the anchor assembly or implant is then positioned and implanted adjacent to a second section of anatomy for the purpose of retracting, lifting, compressing, approximating, supporting or repositioning the second section of anatomy with respect to the first section of anatomy as well as for the purpose of retracting, lifting, compressing, approximating, supporting or repositioning the first section of anatomy with respect to the second section of anatomy. It is also to be recognized that both a first and second portion of the anchor assembly can be configured to accomplish the desired retracting, lifting, compressing, approximating, supporting or repositioning of anatomy due to tension supplied during delivery via a connector assembly affixed to the first and second portions of the anchor assembly or implant.

The delivery device can include an endoscope providing the ability to view the interventional procedure. The delivery device can further include a plurality of projecting needles as well as structure to temporarily compress tissue.

Figure 1:
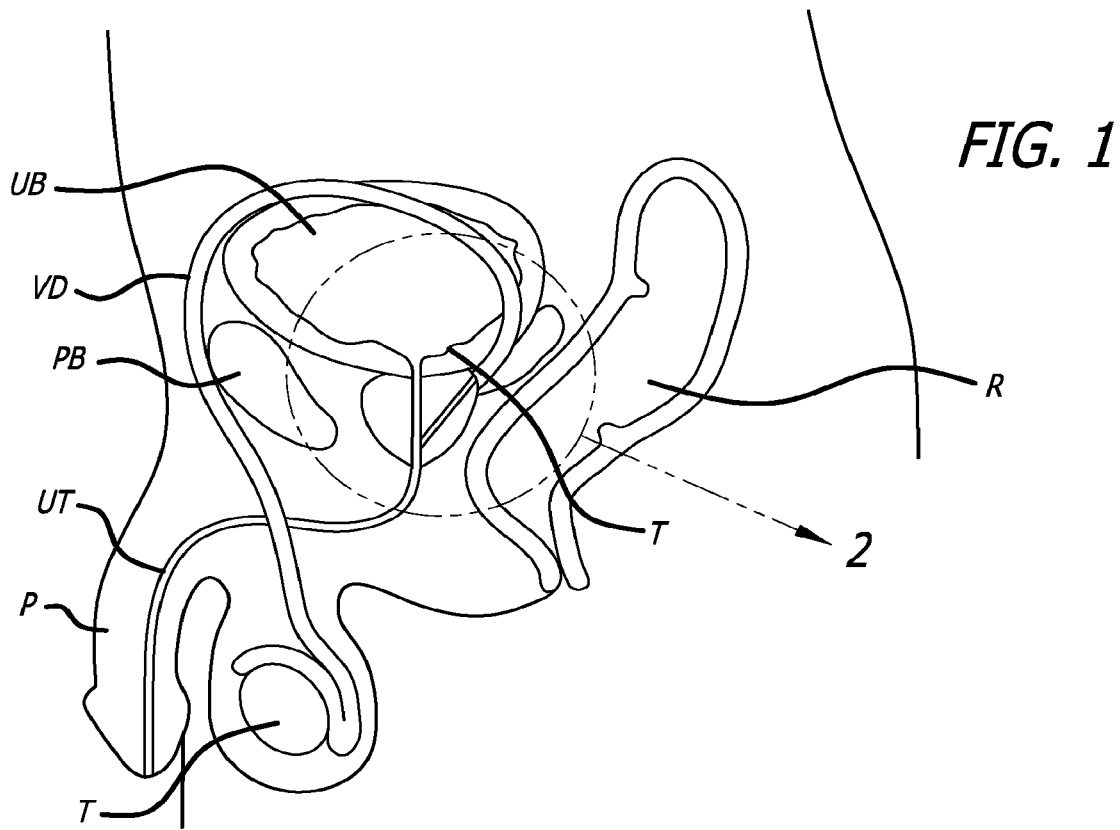
FIG. 1 is a cross-sectional view, depicting anatomy surrounding a prostate in a human subject.
Figure 2:
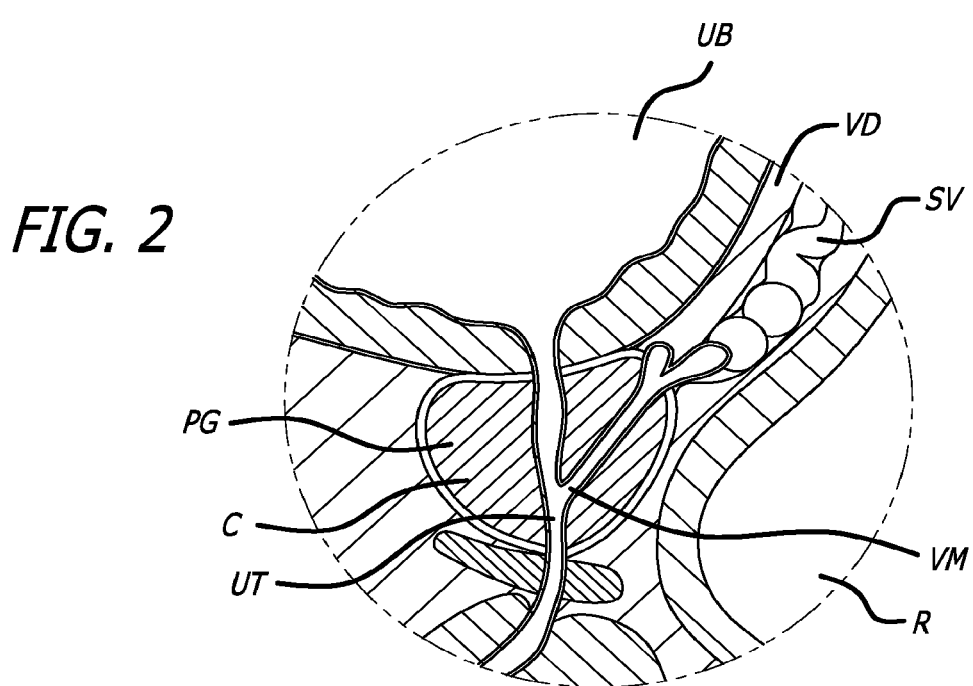
FIG. 2 is an enlarged cross-sectional view, depicting anatomy surrounding a prostate.

With reference to FIGS. 1-2, various features of urological anatomy of a human subject are presented. The prostate gland PG is a walnut-sized muscular gland located adjacent the urinary bladder UB. The urethra UT runs through the prostate gland PG. The prostate gland PG secretes fluid that protects and nourishes sperm. The prostate also contracts during ejaculation of sperm to expel semen and to provide a valve to keep urine out of the semen. A firm capsule C surrounds the prostate gland PG.

The urinary bladder UB holds urine. The vas deferentia VD define ducts through which semen is carried and the seminal vesicles SV secrete seminal fluid. The rectum R is the end segment of the large intestine and through which waste is dispelled. The urethra UT carries both urine and semen out of the body. Thus, the urethra is connected to the urinary bladder UB and provides a passageway to the vas deferentia VD and seminal vesicles SV.

Further, the trigone T is a smooth triangular end of the bladder. It is sensitive to expansion and signals the brain when the urinary bladder UB is full. The verumontanum VM is a crest in the wall of the urethra UT where the seminal ducts enter. The prostatic urethra is the section of the urethra UT that extends through the prostate.

In one embodiment (See FIG. 3), the anchor assembly is embodied in a tissue approximation anchor (TAA). The tissue approximation anchor is an implant assembly that includes one tubular member, referred to as the capsular anchor or, more generally, distal fixture 70. The distal fixture 70 is preferably connected by a suture (preferably polyester) 78 to a slotted, flattened-tubular member (preferably comprised of stainless steel), referred to as the urethral anchor or proximal fixture 84. In one specific, non-limiting embodiment, the distal fixture 70 is comprised of an electropolished Nitinol (nickel titanium alloy SE508, 55.8% nickel) tube. As described below, further embodiments of anchor assemblies are contemplated. Such devices are delivered to an interventional site in a first configuration, and permitted to assume a second configuration to accomplish a desired treatment.

Figure 3:
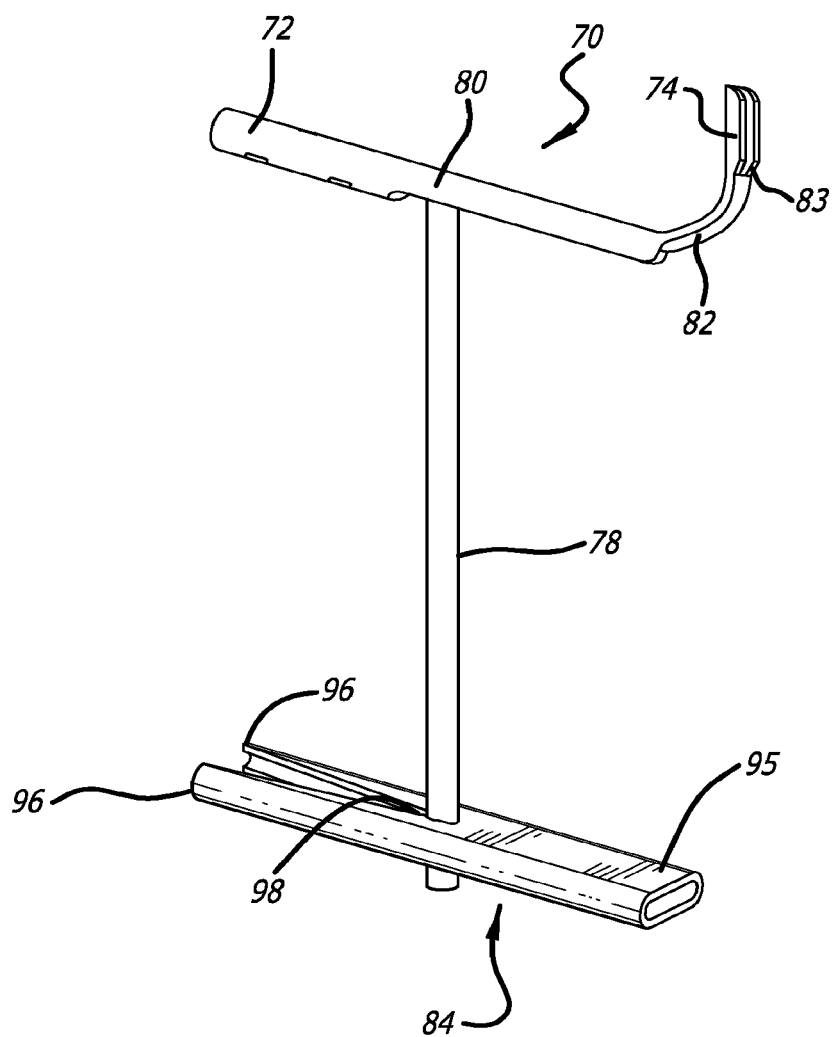
FIG. 3 is a perspective side view, depicting one embodiment of an anchor assembly

The tissue approximation anchor shown in FIG. 3 is designed to be useable in a physician's clinical office environment (in contrast to requiring a hospital environment) with a delivery tool. The delivery tool is used through a 19 Fr sheath in one preferred embodiment, while in another embodiment a sheath size of 21 F is employed. Additionally, the material selection and construction of the tissue approximation anchor still allows for a subsequent TURP procedure to be performed, if necessary, on the prostate. In this suture-based, tissue approximation technique, a needle delivery mechanism is used to implant an anchor assembly. Once the distal anchor assembly has been deployed, with the needle retracted and the anchor assembly is left in opposition with target anatomy.

Figure 4A:
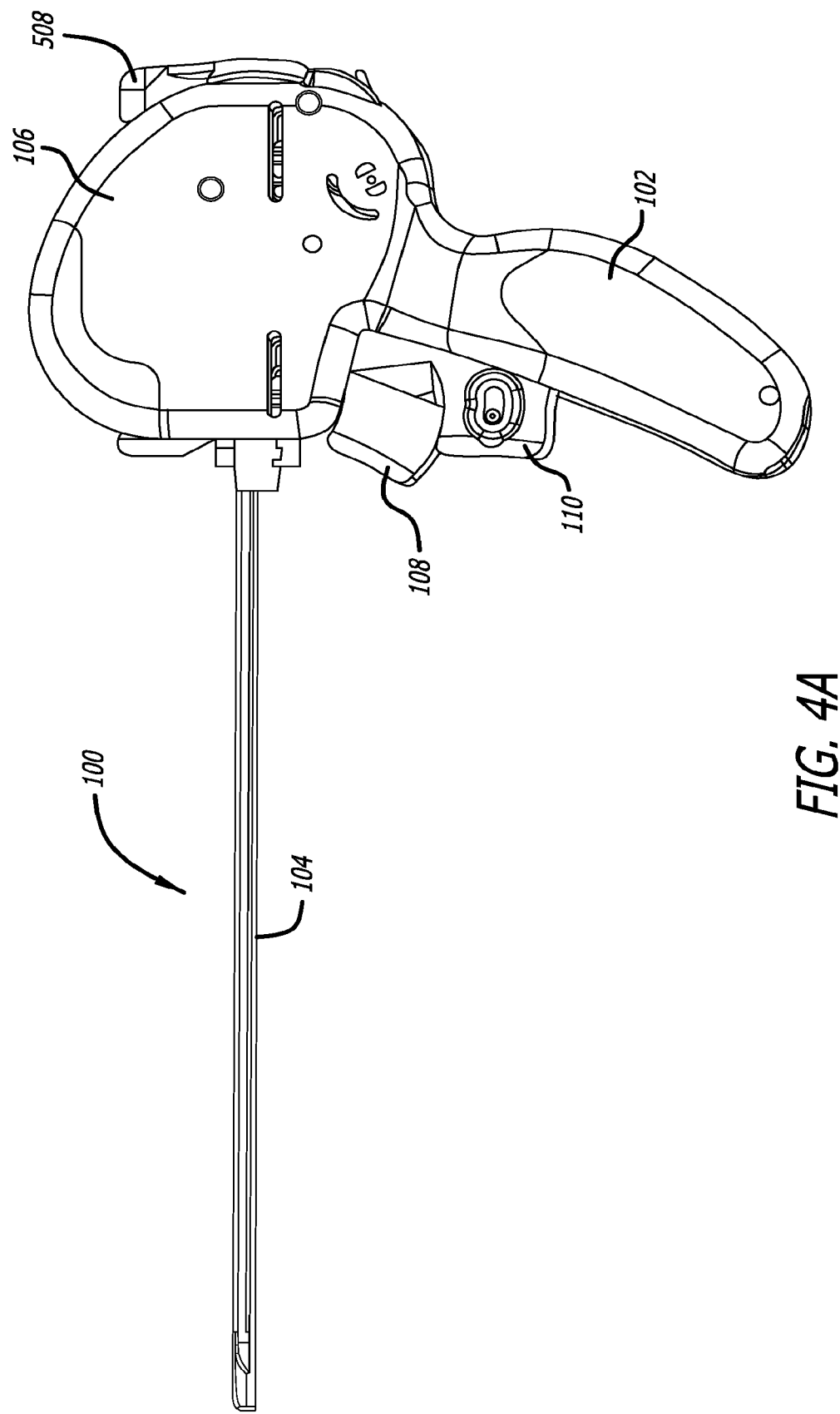
Figure 4C:
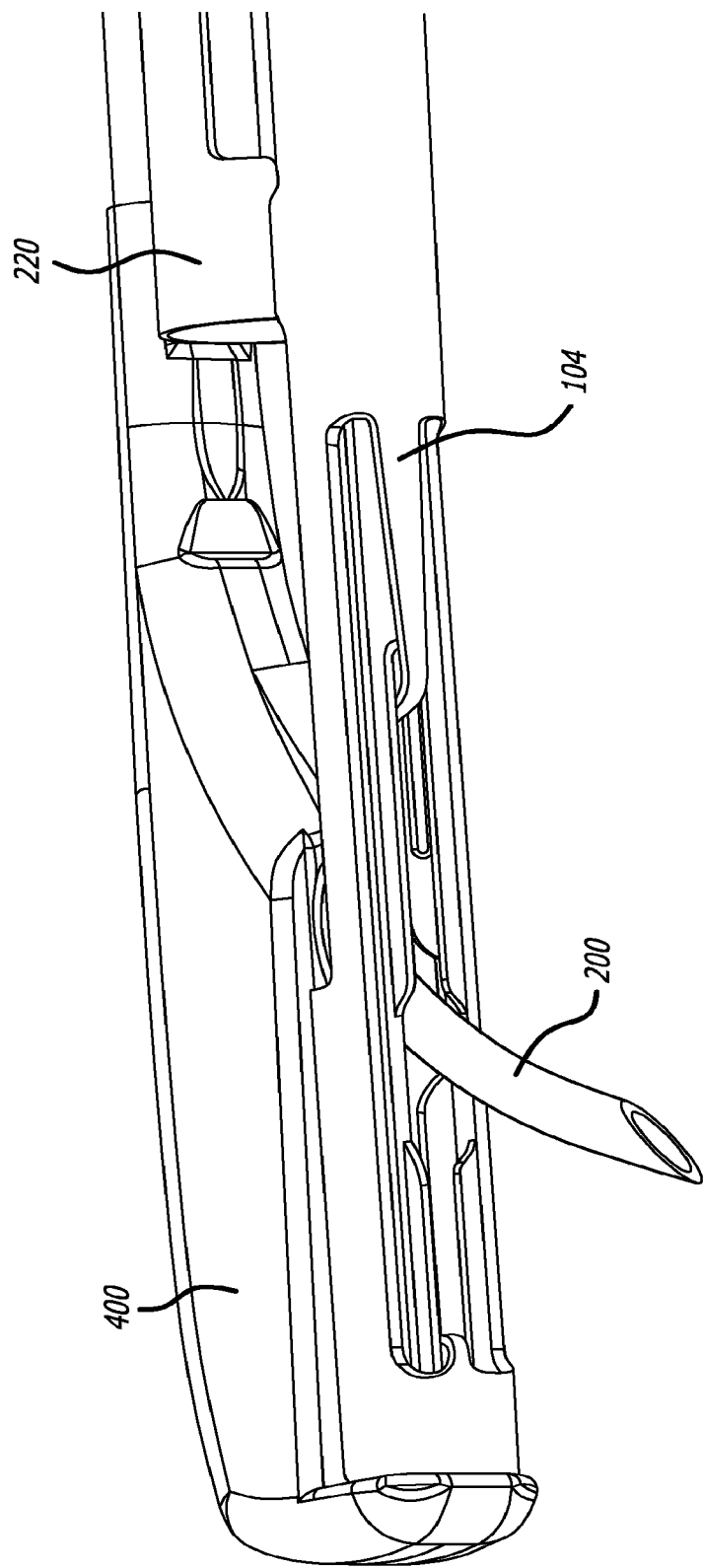

Referring now to FIGS. 4A-C, there is shown one embodiment of a delivery device 100. This device is configured to include structure that is capable of both gaining access to an interventional site as well as assembling and implanting one or more anchor assemblies or implants within a patient's body. The delivery device 100 can be configured to assemble and implant a single anchor assembly or implant a single bodied anchor or multiple anchors or anchor assemblies. The device is further contemplated to be compatible for use with a 19F sheath. The device additionally includes structure configured to receive a conventional remote viewing device (e.g., an endoscope) so that the steps being performed at the interventional site can be observed.

Prior to use of the present device 100, a patient typically undergoes a five day regimen of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to elongate member 104. Elongate member 104 can house components employed to construct an anchor assembly and is sized to fit into a 19F cystosopic sheath for patient tolerance during a procedure in which the patient is awake rather than under general anesthesia. The assembly is intended to include structure to maintain its positioning within anatomy.

The anchor delivery device 100 further includes a number of subassemblies. A handle case assembly 106 including mating handle parts that form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members that facilitate assembly and delivery of an anchor assembly at an interventional site. A needle actuator 108 is provided and as described in detail below, effectuates the advancement of a needle assembly to an interventional site. In one approach, the needle assembly moves through a curved trajectory and exits the needle housing in alignment with a handle element, and in particular embodiments, in alignment with the grip. In various other embodiments, the needle housing is oriented such that the needles exits the housing at either the two o'clock or ten o'clock positions relative to a handle grip that is vertical. A needle retraction lever assembly 110 is also provided and when actuated causes the needle assembly to be withdrawn and expose the anchor assembly.

In one particular, non-limiting use in treating a prostate, the elongate member 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate member 104 is advanced within the patient until a leading end thereof reaches a prostate gland (PG). In a specific approach, the side(s) (or lobe(s)) of the prostate to be treated is chosen while the device extends through the bladder and the device is turned accordingly. The inside of the prostate gland, including the adenoma, is spongy and compressible and the outer surface, including the capsule, of the prostate gland is firm. By the physician viewing with an endoscope, he/she can depress the urethra into the prostate gland compressing the adenoma and creating the desired opening through the urethra. To accomplish this, the physician rotates the tool. The physician then pivots the tool laterally about the pubic symphysis PS relative to the patient's midline.

The delivery device is at this stage configured in a ready state. The needle actuator 108 and the needle retracting lever 110 are in an inactivated position.

Upon depression of the needle actuator 108, the needle assembly 200 (See FIG. 4C) is advanced from within the elongate member 104. The needle assembly can be configured so that it curves back toward the handle as it is ejected. In use in a prostate intervention, the needle assembly is advanced through and beyond a prostate gland (PG). Spring deployment helps to ensure the needle passes swiftly through the tough outer capsule of the prostate without "tenting" the capsule or failing to pierce the capsule. In one approach, the needle is made from Nitinol tubing and can be coated with Parylene N. Such a coating helps compensate for frictional or environmental losses (such as wetness) that may degrade effectiveness of needle penetration.

In a rigid delivery system, the needle assembly 200 uses the rigidity of the elongated shaft of a rigid delivery system to facilitate penetration into the prostate gland and the outer tissue planes. In contrast, a flexible system may not have sufficient rigidity to oppose the force of the needle as it attempts to penetrate the prostate gland. One consequence of this lack of sufficient rigidity in the flexible system may be to reduce the penetration depth of the needle and prevent proper deployment of the anchor.

In some aspects, a counterweight is incorporated into the handle of the delivery device to provide the necessary opposing force during needle penetration. Such an opposing force may prevent or diminish the recoil of the shaft during penetration of the needle into the prostate gland. In some aspects, during penetration of the needle a counterweight in the handle of the delivery device would be accelerated in such a way so as to counteract the torque generated by the action of the needle.

Figure 5:
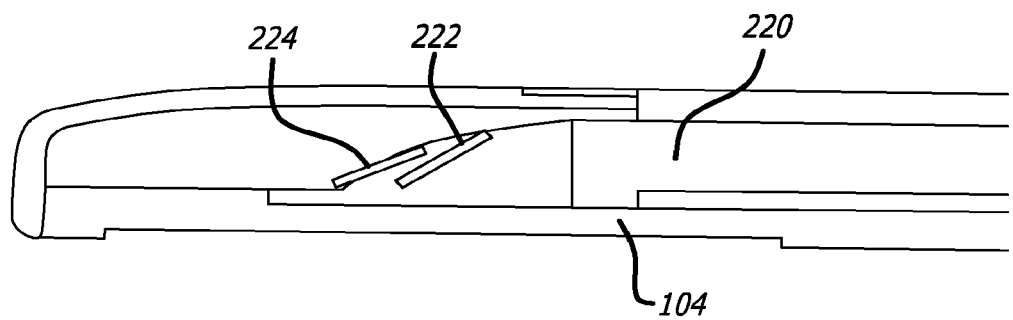
FIG. 5 is an enlarged view, depicting a distal portion of a delivery device including mirrors.

In order to view this operation, the delivery device 100 can be provided with a scope 220. Configured distally to a terminal end of the scope 220 can be one or more mirrors 222, 224 (See FIG. 5). Thus, lateral projection of the needle 200 (See FIG. 4C) can be viewed by the operator via images reflected by the mirrors 222, 224. The mirrors 222, 224 can be positioned to provide a wide field of view for navigation and a narrower field of view for implant delivery. For example, mirror 224 can be positioned and configured with a particular curvature, concavity, or convexity such that the view of the delivery area through the scope 220 is a wide field of view. Similarly in this example, mirror 224 can be positioned and configured with a particular curvature, concavity, or convexity such that the view of the delivery area through the scope 220 is a narrow, and optionally magnified, field of view. In some aspects, the mirrors 222, 224 can be further made to articulate to alter views during the interventional procedure, such as by mounting the mirror on pivots.

The articulation of mirrors 222, 224 can be controlled the operator using any number of suitable methods, including mechanical, electromagnetic, or electromechanical actuation. In one example of mechanical articulation, wires positioned to run at least part of the length of elongate member 104 and connected to at least one of mirrors 222, 224 can be controlled by the operator using levers, dials, triggers, or other control devices to articulate mirrors 222, 224 about their pivots. Alternately, the wires can be controlled by advancing or retracting the scope 220 such that after the scope 220 passes a certain distal point in elongate member 104, scope 220 engages the wires to articulate mirrors 222, 224 about their pivots. In some aspects, mirrors 222, 224 are capable of being articulated individually and in other aspects mirrors 222,224 are articulated in conjunction. In another aspect, the scope 220 can directly engage and articulate one or more of mirrors 222, 224 without a wire or other connecting element between scope 220 and mirrors 222, 224.

In some aspects, articulation of mirrors 222, 224 can be controlled by electromagnetic or electromechanical methods. For example, one or more of mirrors 222, 224 can be electrically connected to one of more controllers accessible to the operator. Such electrical connections can provide current to electromagnets positioned near mirrors 222, 224 such that mirror 222, 224 are magnetically deflected to articulate them about their pivots. Similarly, mirrors 222, 224 can be articulated using electromechanical motors or actuators.

In yet another, alternative embodiment, the scope 220 may include structure facilitating controlled turning or pivoting of a distal portion of the endoscope. Such structures can include the mechanical, electromagnetic, and electromechanical methods described herein or equivalent methods of turning of pivoting a distal portion of the endoscope.

Figure 6:
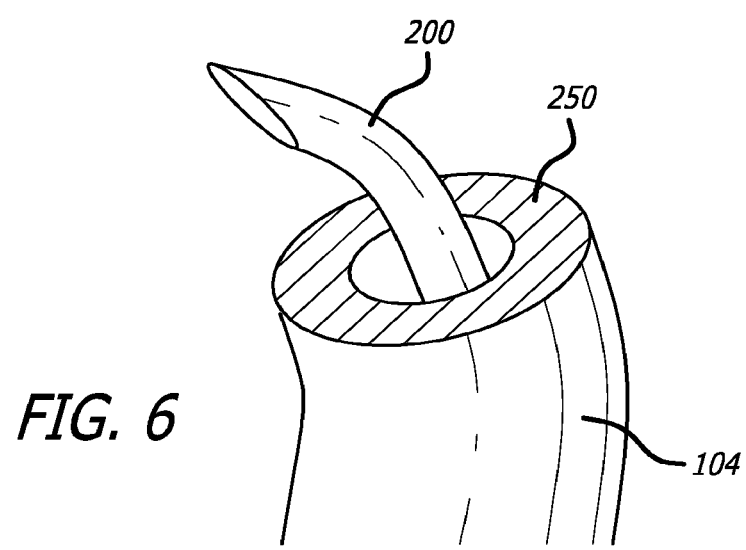
FIG. 6 is an enlarged view, depicting a needle projecting through an annular lens scope.

In one alternate approach (FIG. 6), the scope 220 can terminate with an annular lens 250. The scope 220 would be positioned close to tissue during anchor assembly deployment and withdrawn to provide a wider field of view as required. The annular lens 250 enhances visibility in a flexible system and provides a low profile for the delivery device.

Figure 7:
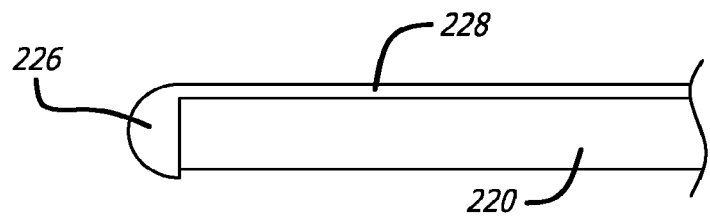
FIG. 7 is a side view, depicting a scope including a liquid filled lens.

As shown in FIG. 7, the scope 220 could further embody a liquid filled lens 226 providing similar functionality. In this regard, a channel 228 is provided along the scope 220 to supply the lens with liquid. Here, the amount of liquid used can be varied to modify the field of view of the scope 220. Without fluid, the field of view will be wider. When fluid is added, the view will be magnified and narrower. Alternatively, the lens can have a flexible distal end which can be changed with low pressure or high pressure fluid which makes the lens either more or less convex and thereby changes the field of view and optionally the magnification. Other liquid lens technology, such as oil and water lenses whose curvature is altered using electrostatic charge thereby changing the field of view and optionally the magnification, are contemplated for use in the flexible implant delivery systems described herein.

Figure 8A:
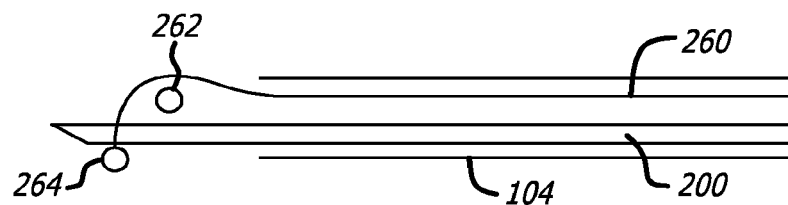
FIGS. 8A-B are each a side view, depicting a flexible elongate member controlled by wires.
Figure 8B:
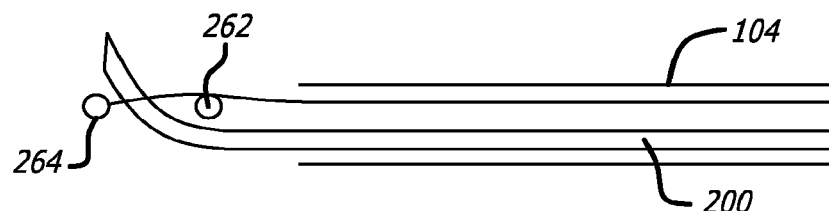

While the elongate member 104 of the delivery device 100 can include a ramp or other structure to direct a needle 200 laterally with respect to the elongate member 104, other approaches can also be employed to achieve this lateral direction. As shown in FIGS. 8A-8B, the delivery device 100 can include a deflection mechanism including drive wire 260 extending longitudinally within the elongate member 104. This approach is characterized by a lower profile, as less room is required to deflect the needle 200 laterally in this fashion. Employing an annular lens endoscope would further reduce the profile of the elongate member 104.

In one approach, the drive wire is routed about a first fixed element 262 and terminates with a connection to a second moving element 264. The needle 200 can be projected distally, between the first and second elements 262, 264 and directly out an opening at a terminal end of the elongate member 104. When placed near an access to anatomical locations nearby orifices or generally transverse surgically created access ports, the drive wire 260 can be pulled proximally a varying amount to set an angle of a distal portion of the needle 220 (See FIG. 8B) for further steps in an interventional procedure. This approach of setting the angle for the needle can be combined with tissue compression approaches described below. By employing a flexible scope that tracks the positioning of the needle 200, the operation can be viewed. It is to be recognized that the fixed and moving elements 262, 264 can be pulleys to minimize friction between moving parts. Moreover, the tip of the needle 200 can be blunted so as to function to push tissue and through the scope, visually observe the effect of subsequent operating steps such as implant positioning or tissue approximating. This blunted needle is used as a pre-needle deployment feature that allows assessment of the ultimate impact of the implant.

Figure 9:
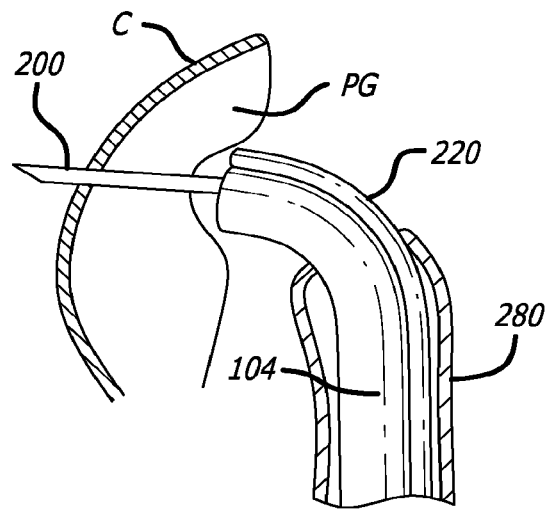
FIG. 9 is a partial cross-sectional side view, depicting use of a flexible delivery device.

A related approach is depicted in FIG. 9 but with this approach, the deflection of the shaft towards the tissue provides compression of the tissue. The delivery device is equipped with a flexible sheath 280 that permits the lateral deflections of the elongate member 104 of a delivery device 100. The flexible scope 220 is mounted longitudinally along the elongate member 104. As the distal section of the elongate member 104 is deflected towards the interventional site, the flexible scope 220 deflects laterally as well. The needle 200 housing an anchor assembly or a portion thereof is projected laterally through tissue such as the prostate. Where the anchor assembly has multiple parts, a second structure of the anchor assembly is contained within the distal end of the elongate member 104 in a position ready for assembly to a first part of the anchor and/or deployment at a proximal location.

Figure 10A:
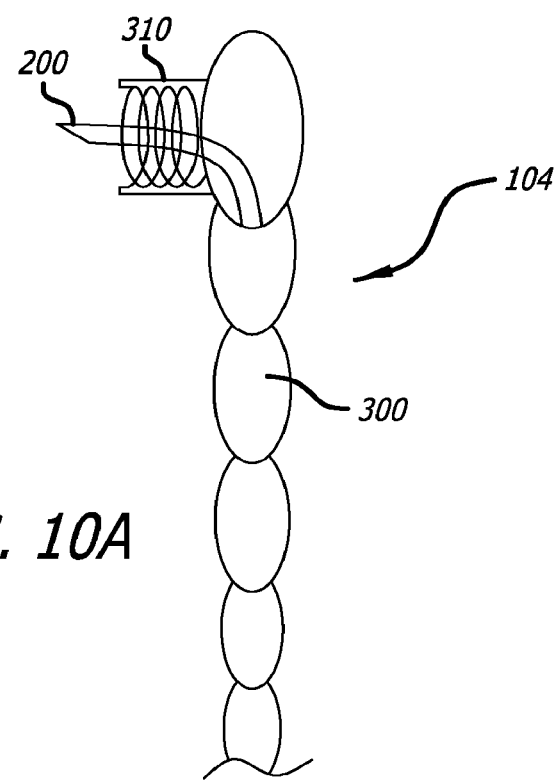
FIG. 10A is a side view, depicting a distal portion of one embodiment of a flexible delivery device.

As shown schematically in FIG. 10A, one approach to providing the elongate member 104 with desired flexibility is to build the elongate member 104 from a plurality of individual sections 300 which thus define a variable deflection structure. Such sections can be tapered at their ends so that one section can pivot with respect to an adjacent section. The delivery device can further include a position stability mechanism that maintains the position of the device within anatomy. A wire configured longitudinally and internal to the sections 300 is arranged to pull the sections 300 into compression to thereby provide tension to hold the overall position of elongate member 104. It is contemplated that the pull wire can be attached to one or more of the segments 300. In this particular embodiment, the distal end of the device can be further equipped with a spring mechanism 310 extending laterally from a distal most section or sections 300. Another pull wire (not shown) is provided and is attached to the spring mechanism 310. Releasing the pull wire functions to control the deployment of the spring mechanism laterally.

In an exemplary procedure, the operator would allow the elongate member 104 to assume full flexibility during insertion within a patient. Once the desired depth of the elongate member 104 is achieved, the wire is pulled to freeze the curved portion of the elongate member 104. The shaft is then positioned against the target tissue such as tissue adjacent the prostate. The tension in the elongate member 104 opposes the force of the spring mechanism 310. The needle 200 is then deployed through the spring mechanism 310 that is compressing tissue, and accesses a distal anchor deployment site. Releasing the pull wire facilitates actuation of the spring mechanism so that such tissue compression is achieved. The pull wire attached to the spring mechanism 310 is then pulled to compress the spring mechanism 310 so that the device can be withdrawn from the site or so that a proximal component of the anchor assembly can be deployed.

Figure 10B:
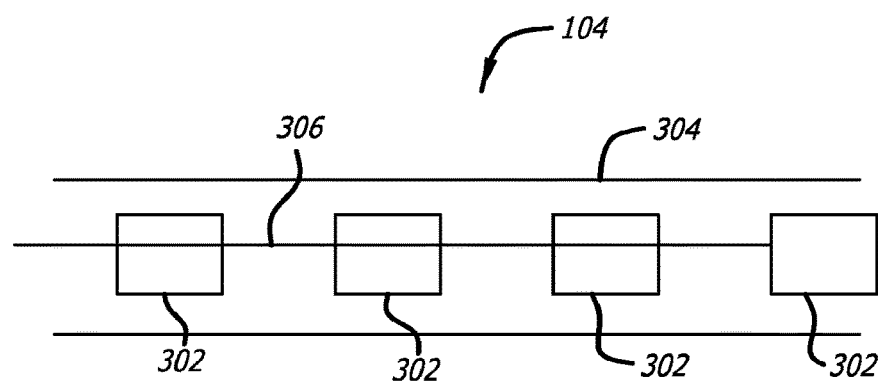
FIGS. 10B-J are various views, depicting alternative approaches to flexible elongate portions.
Figure 10C:
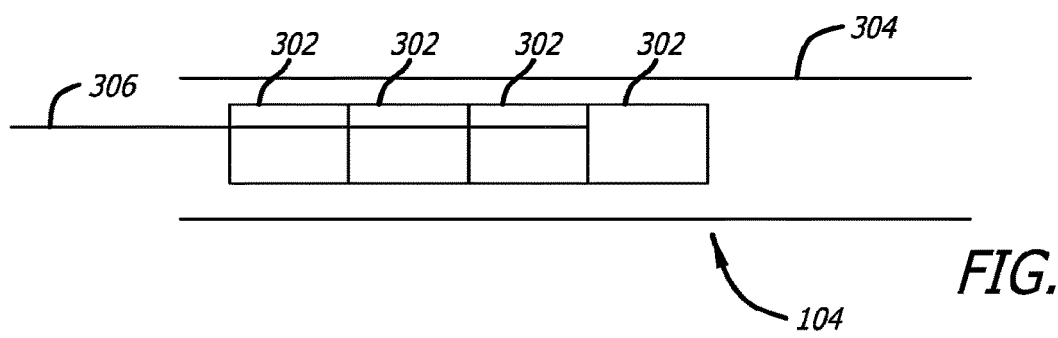
Figure 10D:
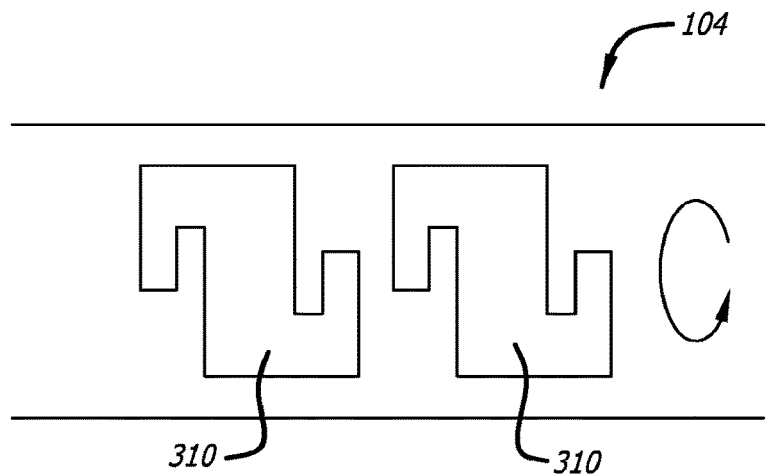

Other approaches to providing the elongate member with desired flexibility are shown in FIGS. 10B-J. As depicted in FIGS. 10B and C, the elongate member 104 can include spaced segments 302 configured within a sleeve 304, the distance between the segments can be controlled by a connecting wire 306. In one embodiment, the connector wire 306 can be threaded through the segments 302 and attached to a leading segment. A proximal segment can define a rigidly positioned platform against which the spaced segments 302 can be withdrawn to a contracted position. Withdrawing the connector wire 306 completely, results in adjacent segments 302 engaging each other. Various degrees of flexibility can be achieved by varying the amount of distance between adjacent segments 302. Further, varying degrees of flexibility can be achieved by varying the geometry of the spaced segments such that the segments have rounded ends, nesting ends, or a combination of such ends. Segments with rounded ends will still retain some flexibility when engaged together while segments with nesting ends will be more rigid when engaged together. Still further, the length of segments can be varied to provide varying degrees of flexibility. Longer segments with less space between adjacent segments will provide more rigidity than short segments with more space between adjacent segments.

In yet another approach (See FIG. 10D), the elongate member 104 can include segments 310 that can assume a spaced relationship, and when twisted or rotated in one direction adjacent segments 310 engage each other to increase rigidity. To return to a higher degree of flexibility the segments 310 are rotated in an opposite direction. Segments 310 may be rotated by control mechanism located in or near the handle of the delivery system.

Figure 10E:
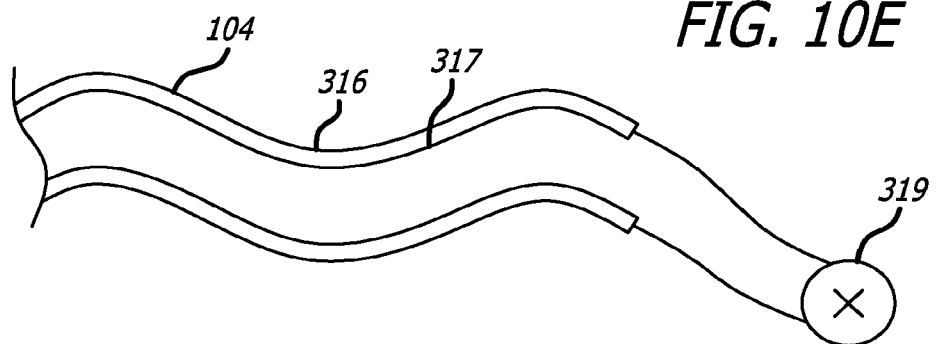
Figure 10F:
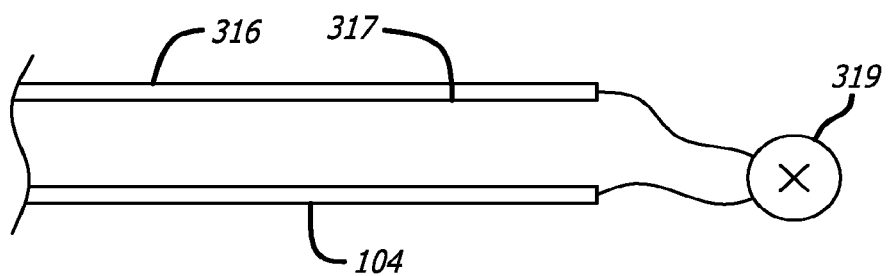

Moreover, as shown in FIGS. 10E and F, the elongate member 104 can be provided with an inflatable shaft 316. In one approach, the shaft 316 can be defined by coaxial tubes or structure 317, 318 to embody inflatable side walls. Here, the elongate member 104 has a first flexibility prior to shaft inflation, and an increased rigidity after inflation from a pump source 319. Variable flexibility can be provided by altering the amount of pressure that is provided to the space between the coaxial tubes. The mechanisms described in FIGS. 10A-F allow variability of flexibility and axial articulation. Another approach for articulation of the flexible shaft is to use a shape memory material. The shaft is set to have a curved or articulated tip at a temperature higher than body temperature and a flexible shape at temperatures at or below body temperature. A heating source (electrical, RF, etc.) is applied causing the tip to articulate and compress tissue after positioned in the anatomy.

Figure 10G:
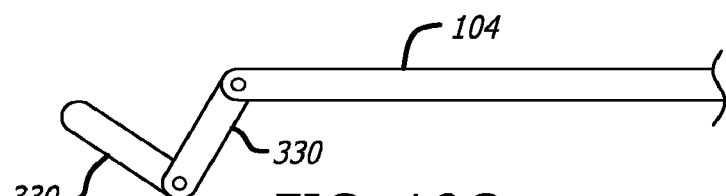
Figure 10H:
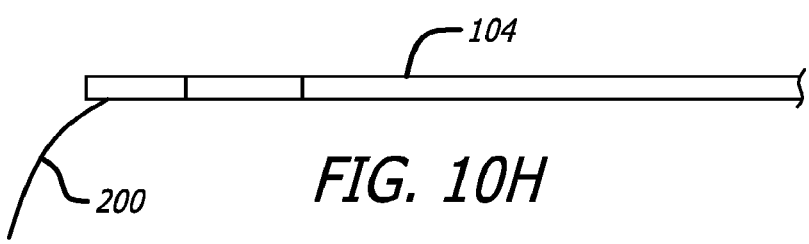

Turning to FIGS. 10G and H, yet another approach to a flexible shaft can be embodied in an elongate member including articulating arms 330 connected at joints having a single degree of rotational freedom. Such arms 330 can be configured to articulate in one plane (FIG. 10G), to the exclusion of another (FIG. 10H). In this way, the elongate member can be stiff in a plane into which a needle 200 is projected to thereby provide necessary support for the projection through tissue.

Figure 10I:
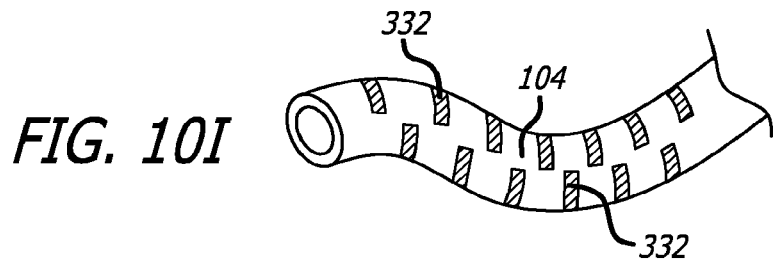
Figure 10J:
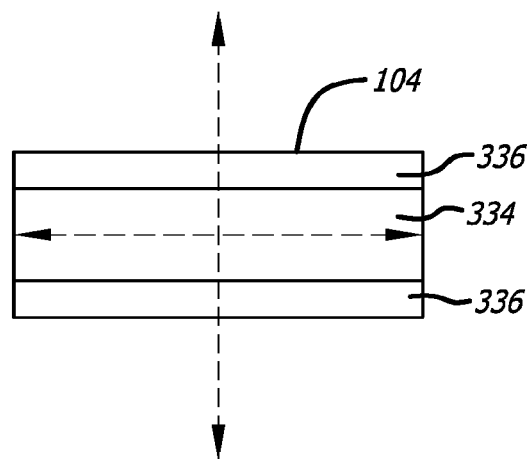

As shown in FIG. 10I, the elongate member 104 can alternatively include a plurality of cut-outs 332 spaced along the member. The cut-outs 332 are configured to allow for flexibility in directions deemed advantageous to a treatment approach. Thus, the cut-outs 332 can be arranged so that the elongate member 104 can be flexible in a single or multiple planes, and along all or portions of a length of the elongate member 104. As depicted in FIG. 10J, the elongate member 104 can further or alternatively include a mixture of less rigid 334 and relatively more rigid 336 materials. These materials can be selected and positioned along distal and/or proximal portions as the shaft to provide desired flexibility.

Figure 11A:
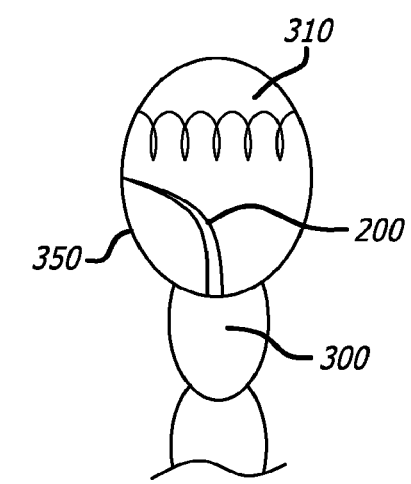
FIGS. 11A-D is a side view, depicting distal portions of alternative embodiments of a delivery device.

In an alternative approach (FIG. 11A), it is contemplated that the needle 200 be preloaded into an expandable tip 350 including a spring mechanism 310 or fluid pressure, shape memory materials or mechanical mechanism. The expandable tip 350 can be employed to maintain positioning and stability of the delivery device within anatomy as well as compress the tissue to open the urethra the desired amount. As the needle 200 is advanced out of the elongate member 104, it triggers release of the expandable tip. It is also contemplated that the expandable tip can lack the spring mechanism 310 but that the advancement of the needle 200 causes the tip expansion.

Figure 11B:
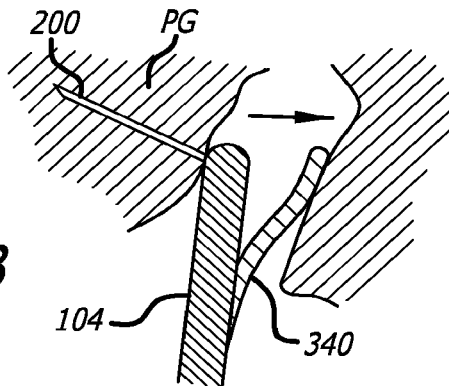
Figure 11C:
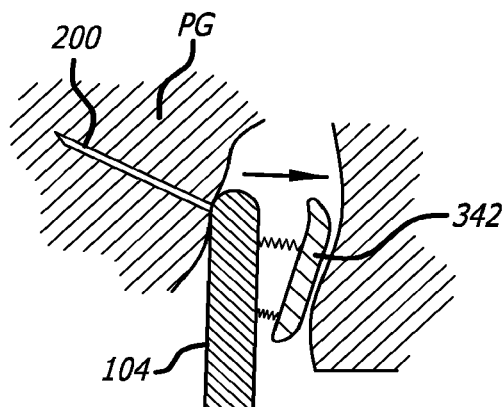
Figure 11D:
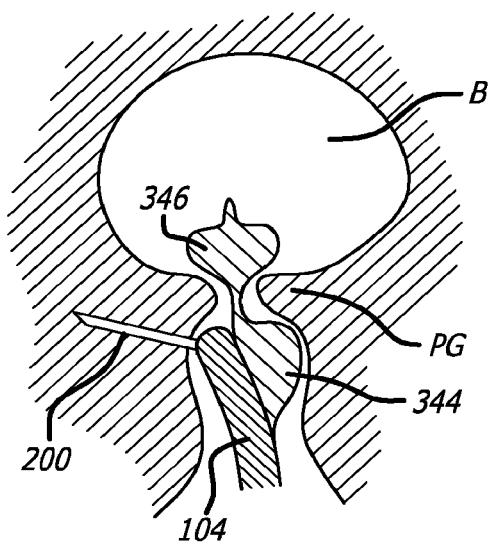

Rather than an expandable tip, the distal end portion of an elongate member 104 can alternatively include an articulating arm 340 configured to maintain positioning and stability (See FIG. 11B). The arm 340 can be controlled to be adjacent the elongate member while the assembly is advanced to a treatment site, and then articulated to apply a force on the prostate gland PG. As shown in FIG. 11C, the elongate member 104 can also include a spring loaded element 342 that is released when it is desired to apply a position maintaining and stability force during an interventional procedure. Moreover, to provide such stability, a balloon assembly can be configured along the elongate member (FIG. 11D). Here, the balloon assembly can include one or both of a first section 344 and a second section 346. When expanded, the first section can function to provide a force to a section of a prostate gland PG. The second section 346 can be expanded within a bladder B to cooperate in maintaining longitudinal positioning of the elongate member 104. Other assemblies for maintaining longitudinal positioning of the elongate member 104 are contemplated, provided that they are reversible and allow for the delivery device to be retracted after delivery of the implant.

Figure 12:
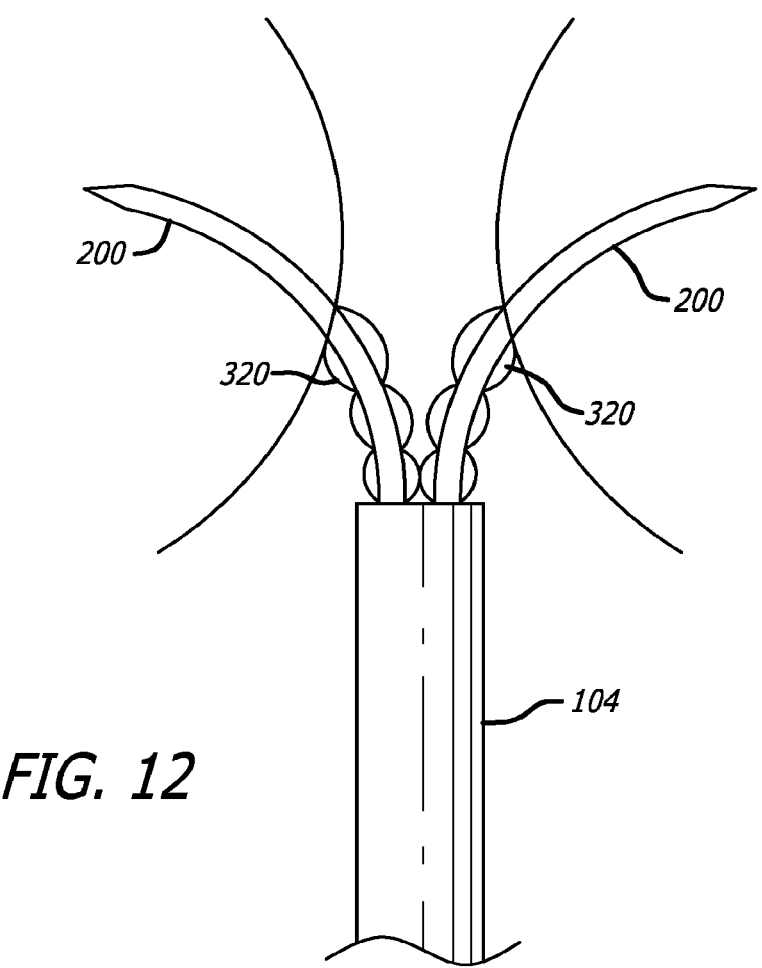
FIG. 12 is a side view, depicting another approach to a delivery device.

In yet a further alternative approach (See FIG. 12), rather than employing an internal mechanism such as a wire to provide tension to the flexible elongate member 104, the delivery device 100 can include two expandable tips 320, through each of which a curved needle 200 is projected. In this way, the elongate member 104 can remain flexible. Here, the activation of the two expandable tips 320 can be simultaneous upon the simultaneous advancement of the needles 200. Such simultaneous deployment may ensure that there are equal and opposite forces against anatomy thereby maintaining positioning of the elongate member 104 within anatomy.

Figure 13A:
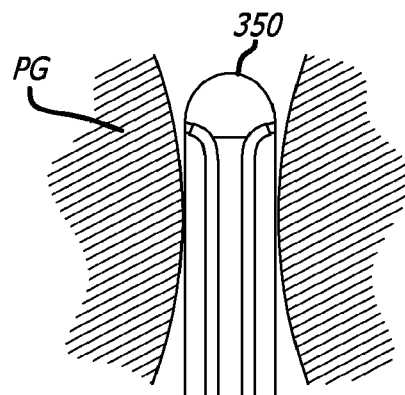
FIGS. 13A-C are partial cross-sectional views, depicting yet further approaches to a delivery devices.
Figure 13B:
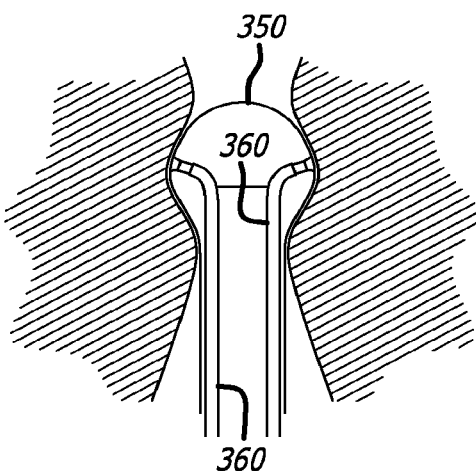
Figure 13C:
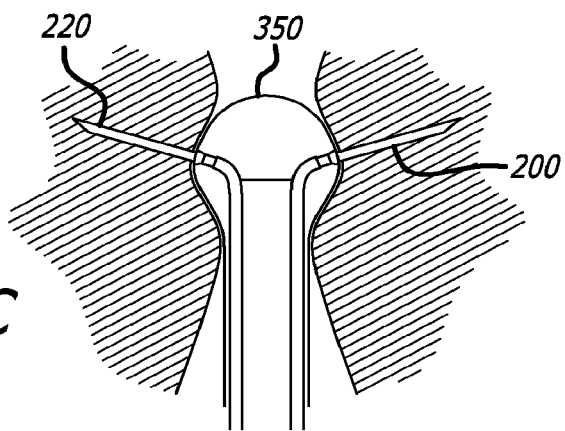

As shown in FIGS. 13A-C, the distal end of elongate member 104 can also include a single expandable tip 350 useable to maintain the positioning of the delivery device 100 within anatomy. The expandable tip 350 is defined by a terminal end of a flexible sheath 352. Again here, two needles 200 are used. Each needle is advanceable through one of a pair of parallel arranged shafts 360. The shafts 360 are articulable or include telescoping structure to expand the tip 350. The needles 200 are then advanced through the expandable tip 350 and placed across targeted anatomy. By causing this to occur simultaneously, the position of the delivery device is maintained and two separate anchor assemblies can be deployed.

Figure 14A:
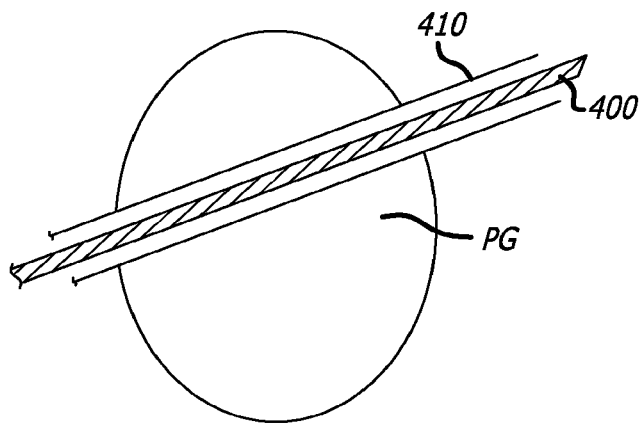
FIGS. 14A-C are partial cross-sectional views, depicting an alternative approach to an anchor.
Figure 14B:
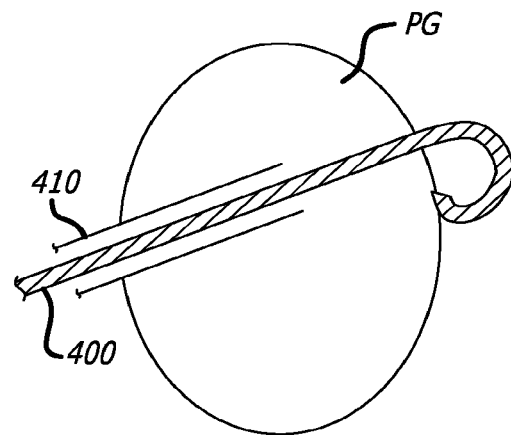
Figure 14C:
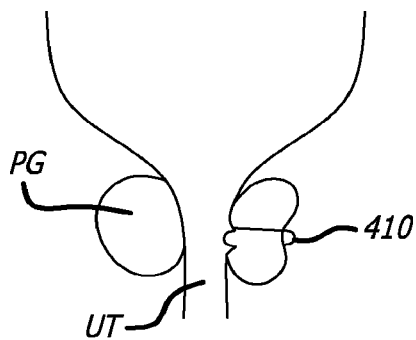

Turning now to FIGS. 14A-C, an alternative anchor 400 is described. This anchor 400 embodies a pointed wire that is held straight by a delivery sleeve 410. The pointed distal end of the wire is employed to form a path through tissue. Once placed as desired within anatomy, such as where a portion of the implant is configured on an outside of a prostate capsule, the delivery sleeve 410 is withdrawn to permit the wire implant 400 to assume its pre-formed configuration. In one aspect, the distal terminal end of the wire implant 400 can be folded so as to direct the pointed end away from engagement with adjacent body anatomy. The implant 400 can be formed from super-elastic material such as Nitinol. Upon delivery of the wire implant 400, a lateral lobe of the prostate gland PG is compressed and the urethra UT is held open (FIG. 14C).

Figure 15A:
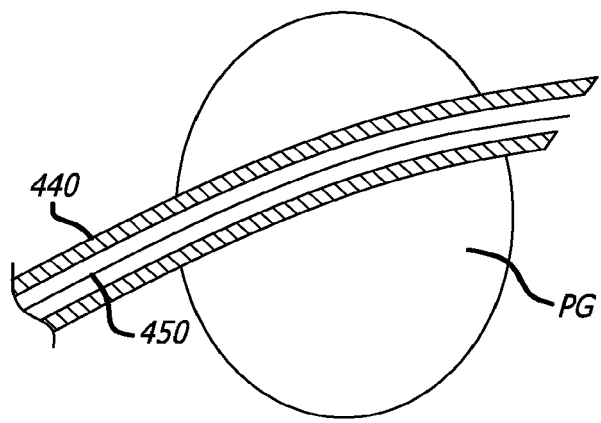
FIGS. 15A-C are partial cross-sectional views, depicting a further alternative approach to one anchor.
Figure 15B:
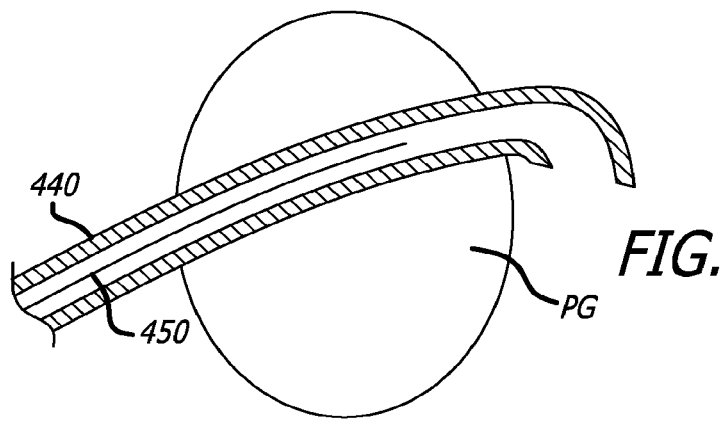
Figure 15C:
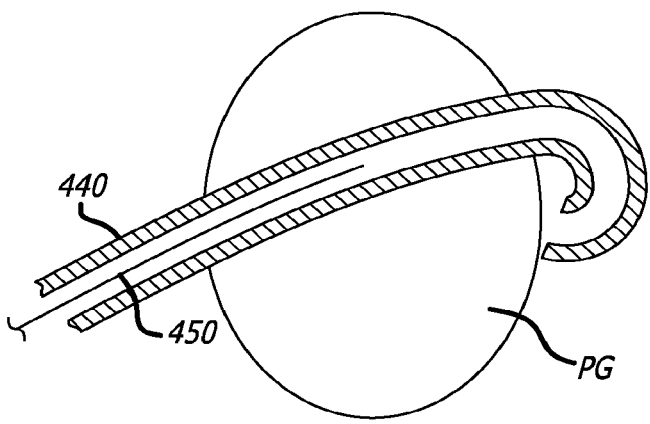

In a related approach (See FIGS. 15A-C), the anchor implant 440 is embodied in a tubular structure and a delivery wire 450 is inserted therewithin to maintain the anchor in a straight configuration for delivery. Once placed as desired within anatomy, the delivery wire 450 is withdrawn to permit the tubular wire implant to assume its preformed configuration. Again, here, upon the completed delivery of the implant 440, the lateral lobe of a prostate gland PG is compressed and the urethra UT is held open.

To treat a prostate (See FIGS. 16A-C) using the implants discussed herein and specifically the aspects of implants described above, the delivery device would first be navigated through the urethra to the prostate. In the straight configuration, the implant would be used to penetrate the lateral lobe of the prostate. Next, the delivery element (i.e. delivery sleeve or wire) would be retracted allowing the implant to assume its preformed shape. Finally, the delivery element would be fully retracted as compression is placed on the prostate. As the implant releases from the tool, this compression is applied against the prostate PG by the implant (FIG. 16C).

Figure 16A:
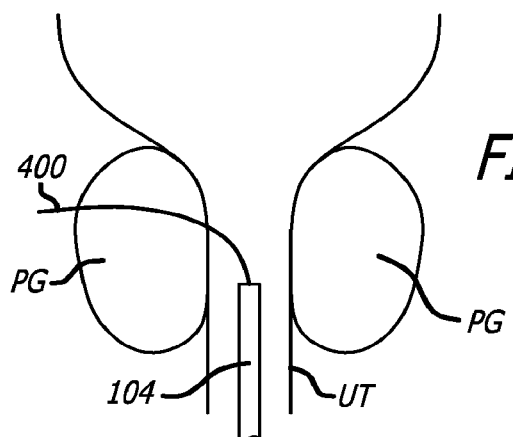
FIGS. 16A-C are partial cross-sectional views, depicting a treatment approach involving an anchor.
Figure 16B:
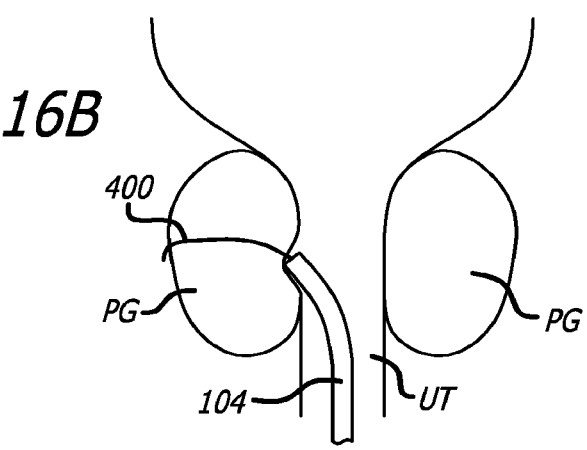
Figure 16C:
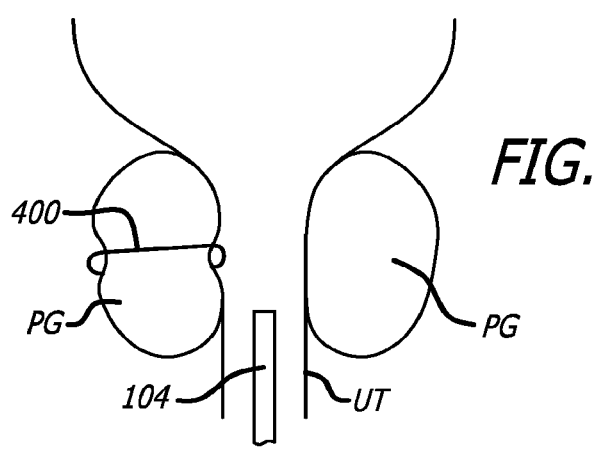

The structure and approach of FIGS. 16A-C can also be employed as a pilot compressing needle. To apply compression to the prostate in a flexible system, the pilot needle would first be deployed through the prostate and capsule. Next, the pilot needle would be used to apply compression to the prostate. A capsular anchor component is then delivered using a second larger needle that is deployed and retracted. Once the capsular component is delivered, the compression needle is released and retracted. Tension would then be applied to the suture, the proximal anchor component or structure implanted such as by engaging it onto the suture, and the suture cut by the device. It is important to note that the pilot needle/wire may need to be formed at a relatively tight radius in order to be delivered without compression on the prostate. A small diameter of the pilot needle/wire will permit manufacturing at such a tighter radius. It is also important to note that the pilot needle may be required to take two different configurations during the implant deployment sequence, one configuration during pilot needle deployment and one configuration during compression.

When using a deployment sleeve, the sleeve would surround the pilot needle/wire during the deployment. The sleeve would keep the needle in the deployment configuration. Once through the prostate capsule, the sleeve can be partially retracted to allow the needle to take a preformed shape suitable for grabbing the prostate during compression. Once a distal component of an anchor assembly has been delivered and compression is released, the sleeve can be repositioned to allow the pilot needle to be retracted.

When utilizing the deployment wire, a wire would be inside a pilot needle during the deployment. The wire would keep the needle in the deployment configuration. Once through the prostate capsule, the wire would be partially retracted allowing the needle to take a preformed shape suitable for grabbing the prostate during compression. After the distal component of an anchor assembly has been delivered and compression is released, the wire is repositioned to allow the pilot needle to be retracted.

Thus, the pilot compression needle concept facilitates utilization of a flexible shaft system consequently reducing or eliminating patient discomfort associated with a rigid shaft system. Moreover, the compression-element design allows either or both a predefined or user-controlled level of tension to be applied to the prostate prior to anchor delivery.

Within a patient's body, the anchor assembly is configured across anatomy within the interventional site. The urethra (UT) is thus widened due to the anchor assembly compressing the surrounding enlarged prostate tissue due to the fact that the outer capsular tissue is rather strong, substantially non-compressible and non-displaceable while the adenoma of the prostate gland is compressible and the urethral wall displaceable.

Figure 17A:
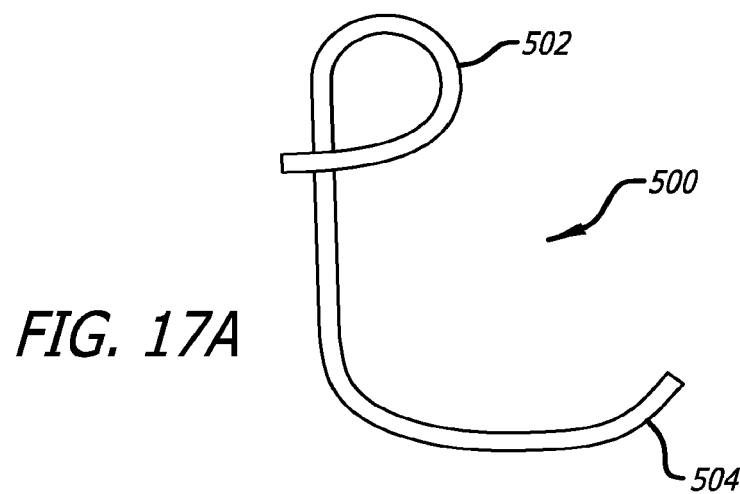
Figure 17B:
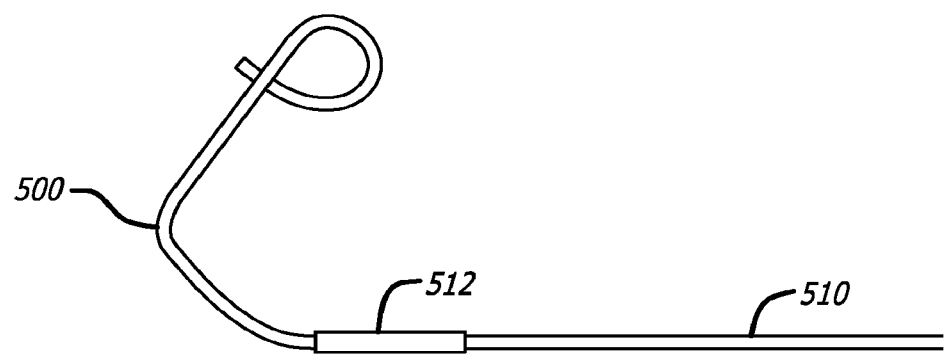

With reference to FIGS. 17A-C, an implant 500 can consist of a single length of elastic or super-elastic shape-memory metal or plastic with a stored state and a deployed state. The stored state is straight or slightly curved while the implant 500 is contained within a delivery needle. The deployed state consists of a straight middle length connecting pre-formed distal and proximal ends. The pre-formed distal end 502 is shaped in a loop or a hook and anchors to the prostatic capsule when treating BPH. The preformed proximal end 504 is shaped as a long bar with a hook, formed at approximately 90 degrees from the middle section of the implant.

One approach to a delivery instrument for the implant consists of a shaft that houses a delivery needle 200. A push rod 510 with a hollow tip 512 is housed within the needle. The proximal end of the implant is pre-loaded into the distal tip 512 of the push rod, and due to the curvature of the proximal end 504 of the implant 500, a given load is required to force the push rod 510 and the implant 500 apart. This load may be tuned by adjusting the curvature of the implant 500 and changing the frictional properties between the push rod 510 and the implant 500. This frictional load determines the tension load at which the implant 500 will be released form the delivery device. The sub-assembly is loaded into the needle with the distal end 502 of the implant stored just proximal to a bevel defining the needle tip and the proximal end of the push rod 510 can be attached to a tensioning element.

In a delivery sequence, a distal tip of delivery instrument is employed to compress tissue. Next, the needle is deployed through tissue. The distal end of the implant is then unsheathed (held in position by the push rod) as the needle retracts. When the needle 200 is retracted back to the delivery device, spring tension is applied to the implant through the push rod. The push-rod to implant interface involves a friction fit that is tuned to release at a specified force (e.g. 1 lb. of tension). When this force is reached, due to the reaction force applied to the distal end of the implant 500 by the prostatic capsule PG, the implant 500 will automatically release from the distal end of the push rod. The proximal end of the implant, which has been stored in a straight configuration in the needle 200, is able to recover its 90 degree bend when it is released from the delivery instrument. The 90 degree leg of the implant creates a local defect along the prostatic urethra.

In contemplated alternative approaches, friction between the needle and the implant can be used to provide tension to the implant, rather than using the hollow-tipped push rod. This would simplify the push rod component, and create a force-controlled implant delivery. Moreover, a second push-rod component or an alternative gripper mechanism can be added to release the implant after retraction of the needle and tensioning of the implant. This would create a distance controlled implant delivery instead of a force-controlled delivery. In this embodiment the implant could have more of a looped proximal end to allow for the treatment of multiple prostate sizes.

Further, the implant 500 could be fabricated from a hybrid of super-elastic metal or plastic and stainless steel so that the proximal portion 515 of the implant is plastically deformable to allow for in-situ implant size variation (See FIGS. 18A-B). Also, a shape memory polymer could be used for the implant. Shape set polymers are as much as two times easier to plastically deform than the same polymers that have not been "programmed" with shape memory. This would allow for easier formability, which would facilitate a less robust and lower profile shaft. Thus, a flexible articulating delivery system could be used, which would provide more direct visibility to the treatment sight and a less traumatic procedure due to the flexible nature of the shaft (See FIG. 9).

Figure 19A:
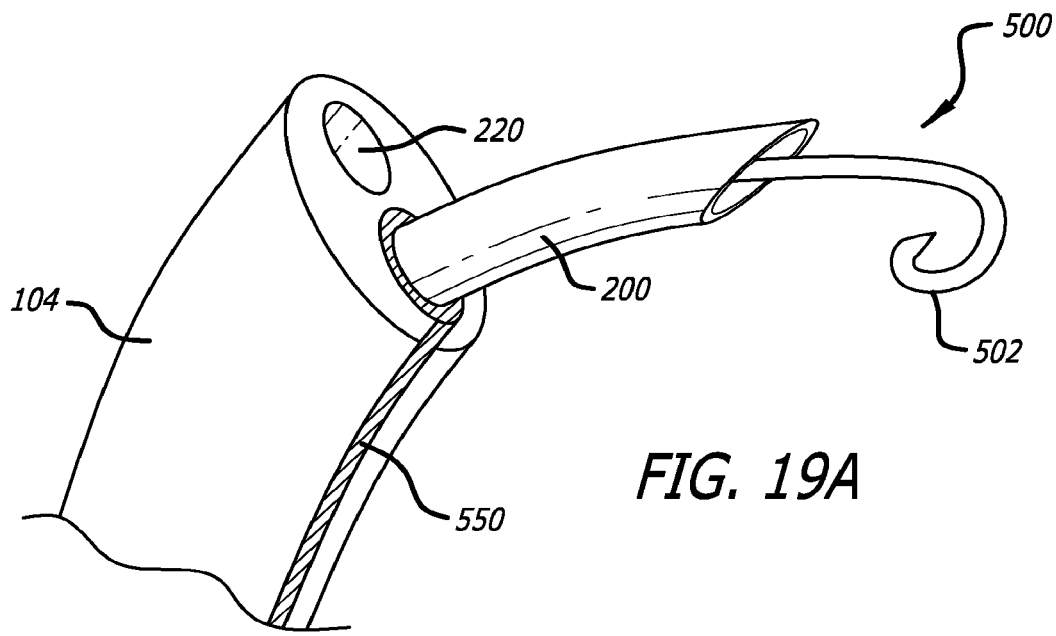
FIGS. 19A-B are perspective and side views, depicting another approach to an implant and delivery system.
Figure 19B:
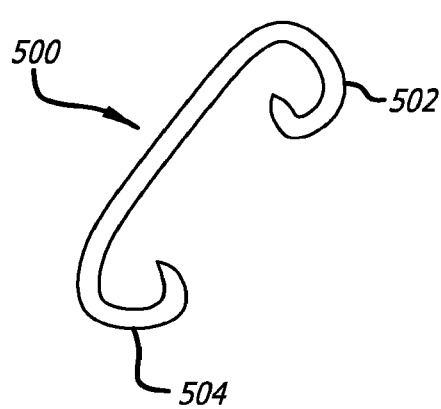

With reference to FIGS. 19A-B, in an alternate embodiment implant 500 includes a shape memory material, such as the metals or plastics described herein or their equivalents. Distal end 502 of implant 500 is preformed to provide distal anchoring features, such as curvature, spirals, hooks, loops, and the like. Implant 500 can be loaded into delivery needle 200 in a low profile configuration and deployed using the delivery methods described herein, namely a push-rod interface. Alternately, implant 500 can be a wire that extends proximally within the delivery device such that it can be advanced directly via the delivery tool, eliminating the need for a separate push-rod or similar element. After distal end 502 of implant 500 bridges the outer tissue planes of the prostate gland via delivery needle 200, delivery needle 200 is retracted, unsheathing at least distal end 502 such that its anchoring features are positioned and implanted adjacent the outer tissue planes of the prostate gland. Tension can be applied to implant 500 as described herein and cutting mechanism 550 severs implant 500 at a point that allows a proximal end 504 of implant 500 to hold tissue in an altered configuration. Proximal end 504 maybe be shape set during manufacturing such that when the residual length of implant 500 is severed, proximal end 504 anchors the urethral side of the prostate gland. Proximal end 504 may be shape set to assume a curved configuration or other configuration that provides such and anchoring feature. One of the benefits of such a shape set embodiment of proximal end 504 is that proximal end 504 may not need to be actively deformed or shaped to provide anchoring features. Another benefit of the aspects of implant 500 in which distal end 502 and proximal end 504 are shape set is that such an implant is effectively customized to a particular anatomy in-situ with little additional operator manipulation of implant 500. In certain aspects of this embodiment, implant 500 could be manufactured with a series of notches or necked areas in proximal end 504 that would facilitate the step of severing implant 500. In some aspects, such notches or necked areas could facilitate shearing of proximal end 504 by twisting or other means such that implant 500 is not severed. Further, such shearing could be accomplished without notches or necked areas.

Figure 20:
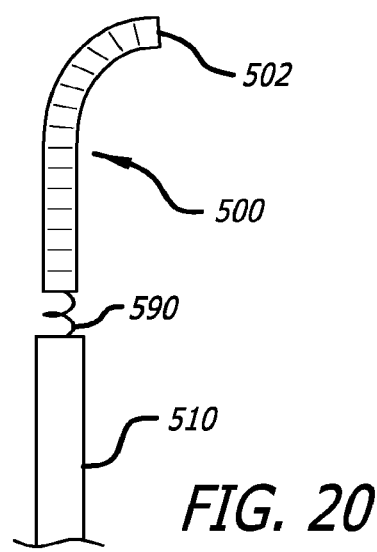
FIG. 20 is a side view, depicting another approach to an implant and delivery system.

With reference to FIG. 20, in an alternate embodiment implant 500 includes a flexible, single-piece device capable of coiling and retracting. In some aspects, implant 500 can be made from a coiled tube or a serrated tube. In some aspects, implant 500 can include a coiled wire and the coiled wire can be wrapped in a shrink-wrap material. In these aspects, implant 500 can be formed from a shape memory material, such as the metals or plastics described herein or their equivalents. Alternately, implant 500 can be formed from conventional metals or plastics provided that it is formed in a way that facilitates coiling or retracting of the implant subsequent to deployment. In some aspects, implant 500 is connected to push rod 510 via wire 590. Wire 590 can be connected to implant 500 and push rod 510 by soldering, welding, or similar connecting method. Implant 500 can deployed by disconnecting implant 500 from push rod 510. In some aspects, implant 500 is disconnected by twisting push rod 510 with respect to wire 590 until wire 590 shears off and disconnects from push rod 510. In some aspects, the joint between push rod 510 and wire 590 is stronger than the joint between wire 590 and implant 500. In such aspects, wire 590 and push rod 510 twist with respect to implant 500 and the wire 590 shears at a point closer to implant 500 than push rod 510. The point at which wire 590 shears can be selected by the design of wire 590, such as by including notches, points of weakness, kinks, or other features that will preferentially shear prior to other sections of wire 590 and/or prior to joints connecting wire 590 with implant 500 and push rod 510. In some aspects, deployment can be accomplished electrically such that wire 590 becomes disconnected from implant 500 or push rod 510 by passing current through wire 590. Wire 590 may include segments or joints of increased resistivity compare with the rest of wire 590 such that wire 590 "fails" at a predictable point when electric current is passed across the segment or joint. In some aspects, electrical wires running with push rod 510 are connected to the joint between wire 590 and push rod 510 and such joint is designed to "fail" when current is run across it. In some aspects, distal end 502 of implant 500 has anchoring features. The aspects and embodiments of implant 500, push rod 510, and wire 590 described with reference to FIG. 20 can be combined with the delivery devices described herein, including the devices using a delivery needle.

With reference to FIGS. 21A-D, in some aspects prosthesis 700 is placed within urethra UT, and more specifically within the prostatic urethra. Prosthesis 700 may be permanent or non-permanent. In non-permanent applications, prosthesis may be resorbable or degradable. Prosthesis 700 may be designed to resorb or degrade, or have its resorbing or degrading triggered, by exposure to urine, body temperature, chemical agents, light, thermal energy, and/or time. In some aspects, prosthesis 700 may be a low-profile device capable of being expanded within urethra UT upon deployment. In some aspects, prosthesis 700 stays in place in urethra UT by engaging the wall of urethra UT with a friction fit and/or by engaging anatomical features in the end of urethra UT, such as the bladder neck, verumontanum, or external sphincter. Prosthesis 700 is capable of providing temporary and/or permanent relief of symptoms by compressing prostate gland PG and/or opening urethra UT. Prosthesis 700 is preferably and advantageously used with a flexible delivery system.

Figure 21A:
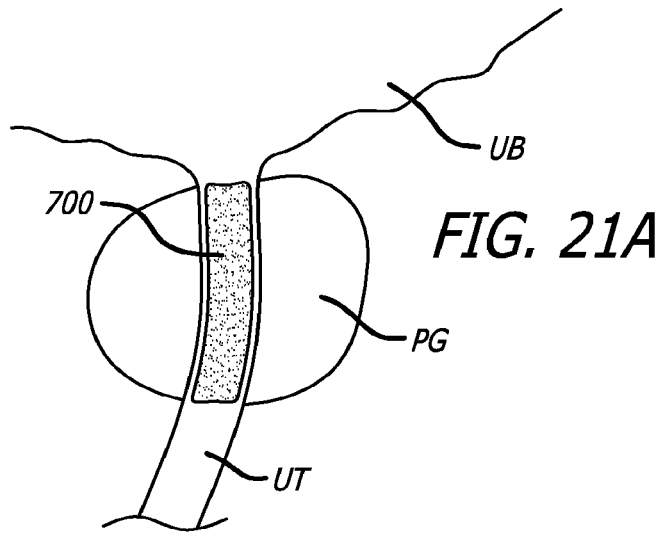
FIGS. 21A-D are a partial cross-sectional side view and a cross-sectional side view, depicting use of a flexible delivery device and implants.

With reference to FIG. 21A, prosthesis 700 may include a pre-formed foam structure. The foam structure may be semi-rigid or rigid, and a single prosthesis may include both semi-rigid and rigid ends or ends of varying rigidity. The foam structure may be open-cell or closed-cell, and a single prosthesis may include both open-cell and closed-cell ends. In some aspects, prosthesis 700 may be delivered in a compressed, low-profile configuration that is capable of expanding to an uncompressed or expanded configuration at the appropriate location in urethra UT. In some aspects, constraining members hold prosthesis in its compressed configuration and such constraining members are removed in order to deploy prosthesis 700. The uncompressed and/or expanded foam structure of prosthesis 700 provides relief of BPH symptoms.

Figure 21B:
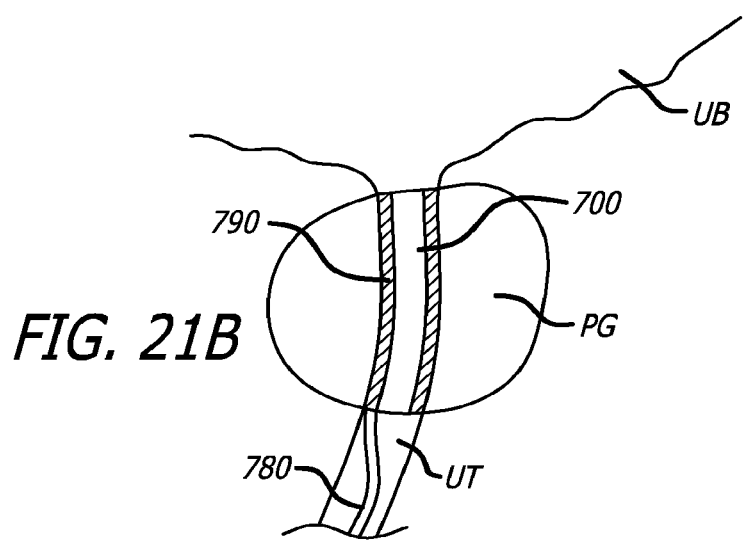
Figure 21C:
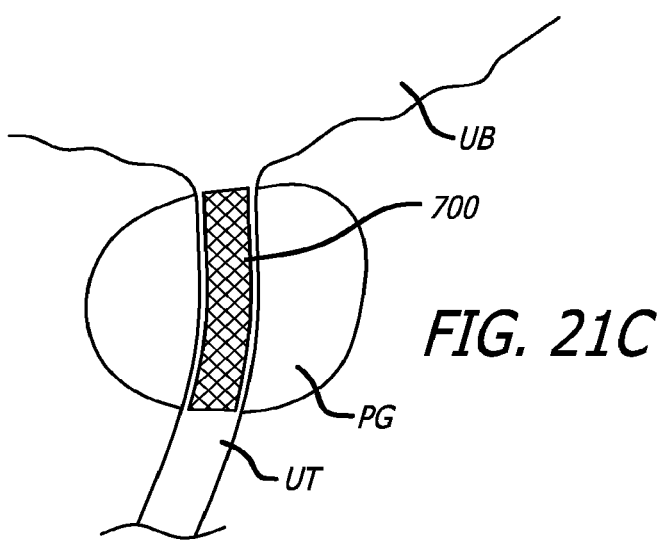

With regard to FIG. 21C, in some aspects prosthesis 700 includes an expandable mesh structure. The mesh structure can be made from metals or plastics, including shape-memory metals and shape-set plastics. In some aspects, the mesh structure of prosthesis 700 is resilient and capable of being reversibly compressed by constraining members. In some aspects, the mesh structure of prosthesis 700 is capable of being expanded by shortening or lengthening prosthesis 700. In some aspects, the mesh structure of prosthesis 700 is capable of being expanded by an expansion member, such as a balloon.

Figure 21D:
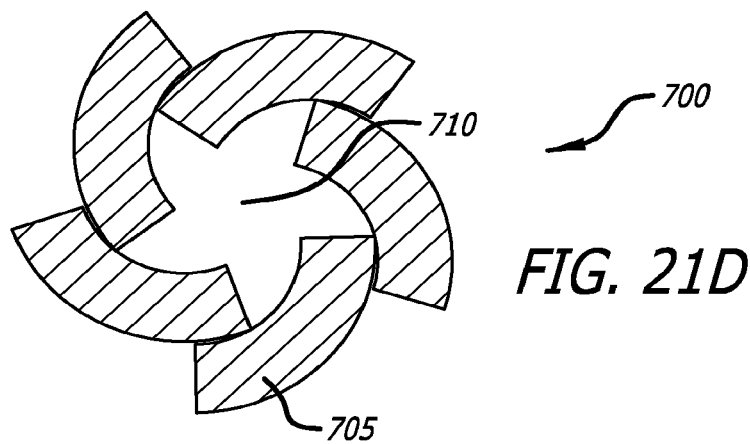

With regard to FIG. 21D, in some aspects prosthesis 700 includes an expandable structure with overlapping sections 705. Overlapping sections 705 define a space inside prosthesis 700, referred to as lumen 710 of prosthesis 700. Overlapping sections 705 are capable of sliding or moving past one another about a tangent to lumen 710 and such motion causes the overall cross-sectional profile of prosthesis 700 to increase and engage urethra UT. Overlapping sections 705 may be made of a metal or plastic, including shape-memory metals and shape set plastic. Overlapping sections 705 in a single prosthesis may be made from the same material or from different materials. The choice of materials may be used to control the rigidity of prosthesis 700 and its expansion characteristics.

With regard to FIG. 21B, in some aspects prosthesis 700 is formed in-situ by delivering a material to urethra UT via insertion device 780. In some aspects, material to form prosthesis 700 in-situ can be inserted into pre-formed shell 790. First, pre-formed shell 790 can be compressed to have a low profile and then delivered to urethra UT and allowed to decompress. Insertion device 780 can then be used to fill pre-formed shell 790 with a material that increases the rigidity of pre-formed shell 790. Such a material can cure into rigid or semi-rigid foam.

Figure 22A:
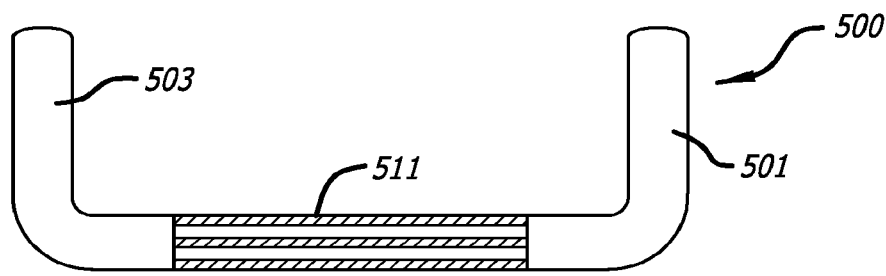
FIGS. 22A-C are side views and a partial cross-sectional side view, depicting another approach to an implant.
Figure 22B:
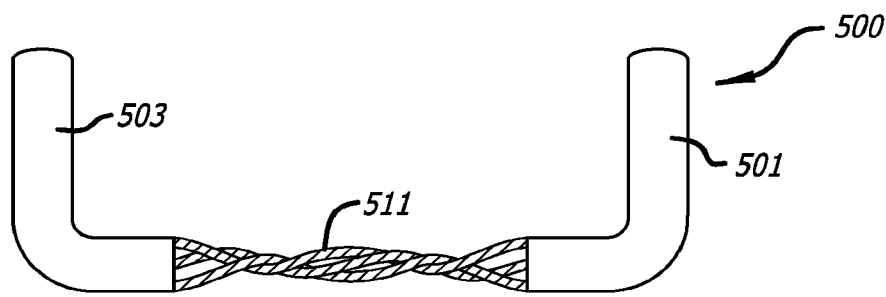

With regard to FIGS. 22A-B, in some aspects implant 500 includes proximal anchor 501, distal anchor 503, and connectors 511. Proximal anchor 501 and distal anchor 503 are pre-formed to include anchoring features that facilitate attachment to tissue. Distal anchor 503 may contain sharp edges or cutting surfaces or other features to facilitate penetration of implant 500 through tissue. Proximal anchor 501 and distal anchor 503 may be wires, tubes, or other low-profile shapes that are also capable of being deformed or shaped to create a bend or other anchoring feature. Proximal anchor 501 and distal anchor 503 may be formed from metals or plastics, including shape-memory metals and shape-set plastics. Connectors 511 include one or more fibers or wires and are connected with proximal anchor 501 and distal anchor 503 using methods such as bonding, friction fitting, melting, tying and the like. FIG. 22B depicts an aspect in which connectors 511 and proximal anchor 501 have been twisted with respect to distal anchor 503. Such twisting decreases the distance between proximal anchor 501 and distal anchor 503 and facilitates the compression of the prostate gland.

Figure 22C:
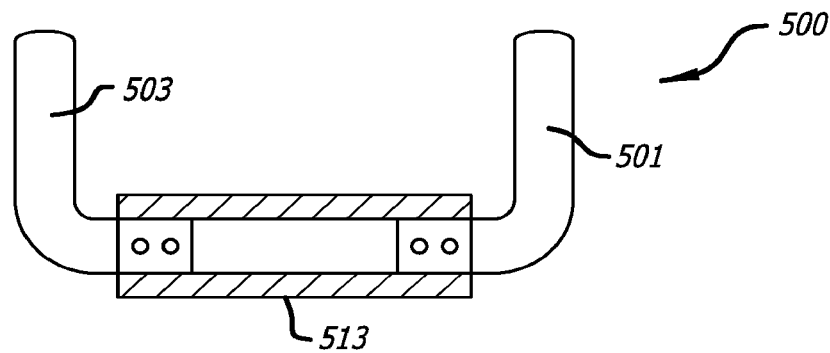

With regard to FIG. 22C, in some aspects connecting tube 513 can connect proximal anchor 501 and distal anchor 503. Connecting tube 513 may be formed from plastic tubing or a similar material that is capable of elastic or semi-elastic axial stretching. The elastic or semi-elastic nature of connecting tube 513 facilitates holding an altered configuration of the prostate gland when distal anchor 503 and proximal anchor 501 have been placed about prostate gland PG as described herein. Proximal anchor 501 and distal anchor 503 are pre-formed to include anchoring features that facilitate attachment to tissue. Distal anchor 503 may contain sharp edges or cutting surfaces or other features to facilitate penetration of implant 500 through tissue. Proximal anchor 501 and distal anchor 503 may be wires, tubes, or other low-profile shapes that are also capable of being deformed or shaped to create a bend or other anchoring feature. Proximal anchor 501 and distal anchor 503 may be formed from metals or plastics, including shape-memory metals and shape-set plastics.

Figure 23A:
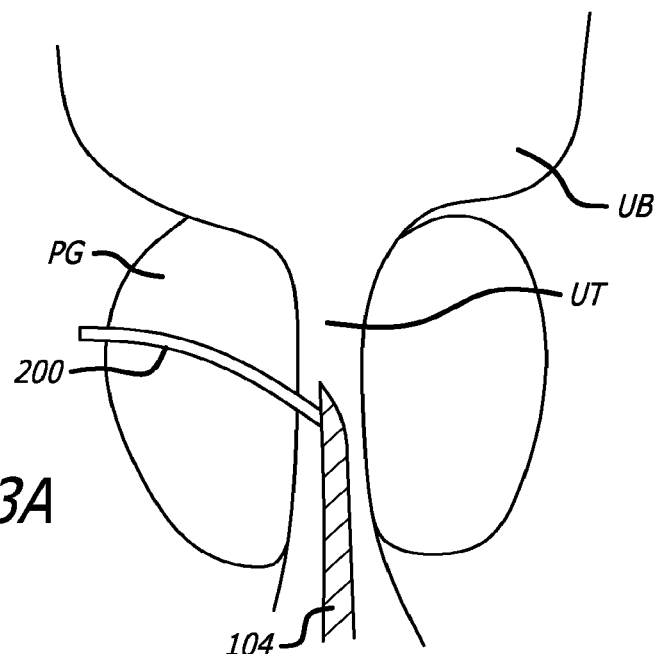
FIGS. 23A-B are partial cross-sectional side views, depicting use of a flexible delivery device and implants.
Figure 23B:
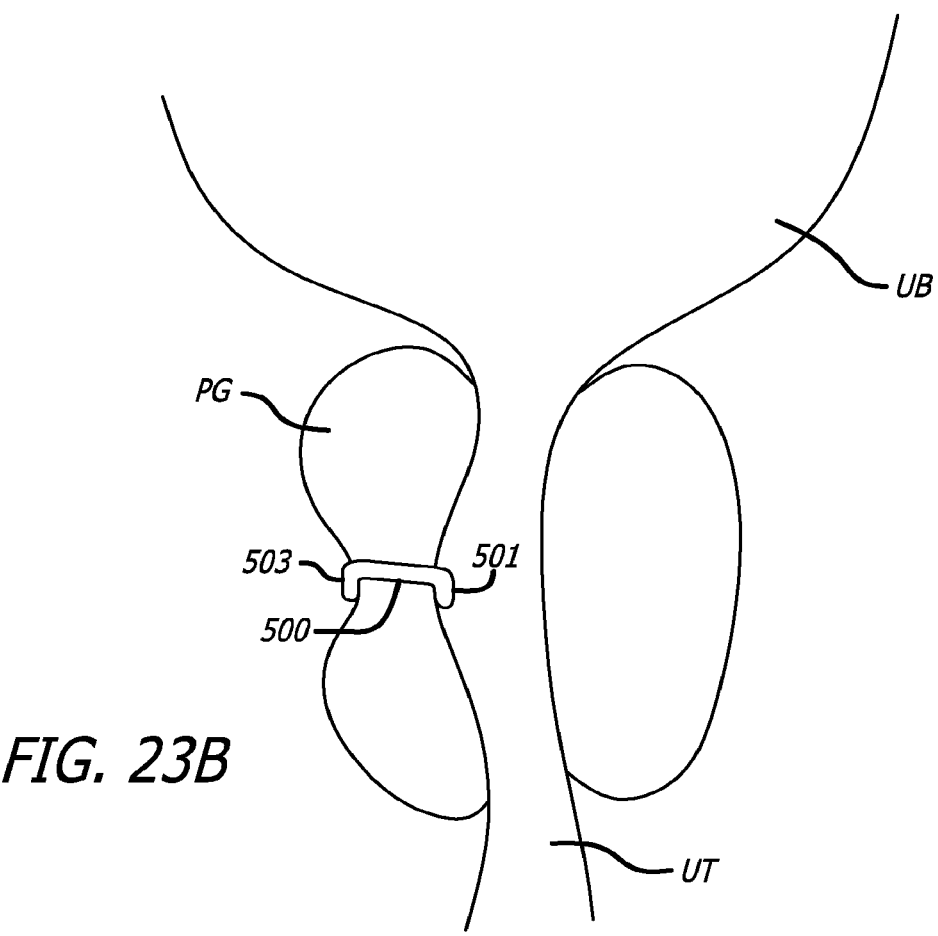

FIGS. 23A-B depicts an aspect in which implant 500 of the type depicted in FIGS. 22A-C are implanted in and facilitate compression of prostate gland PG. Elongate member 104 is advanced into urethra UT and into position in the prostatic urethra. Delivery needle 200 is used to penetrate prostate gland PG and provide access to the outer tissue planes of prostate gland PG. Optionally, the cutting or piercing surfaces of implant 500 may also facilitate penetration of prostate gland PG. Delivery needle 200 is retracted and distal anchor 503 of implant 500 anchors to the outer tissue planes of prostate gland PG. As delivery needle 200 is further retracted, proximal anchor 501 attaches to tissue. In some aspects, proximal anchor 501 and connectors 511 are twisted with respect to distal anchor 503 to hold an altered configuration for a variety of sizes of prostate glands. In some aspects, the elasticity of connecting tube 513 holds an altered configuration for a variety of sizes of prostate glands.

Figure 24A:
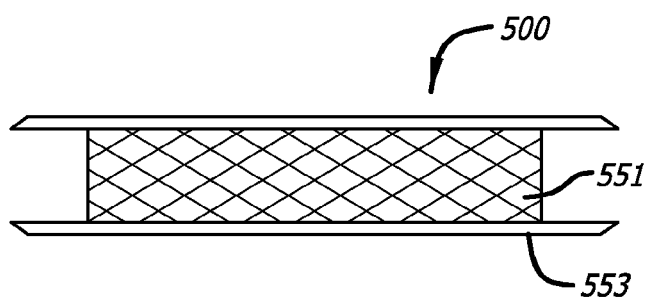
FIGS. 24A-D are side views and partial cross-sectional side view, depicting another approach to an implant and delivery system.
Figure 24B:
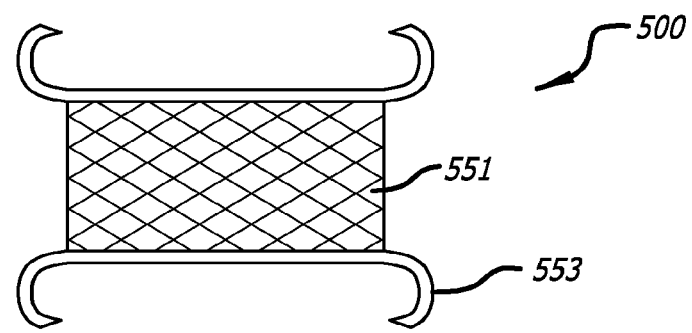
Figure 24C:
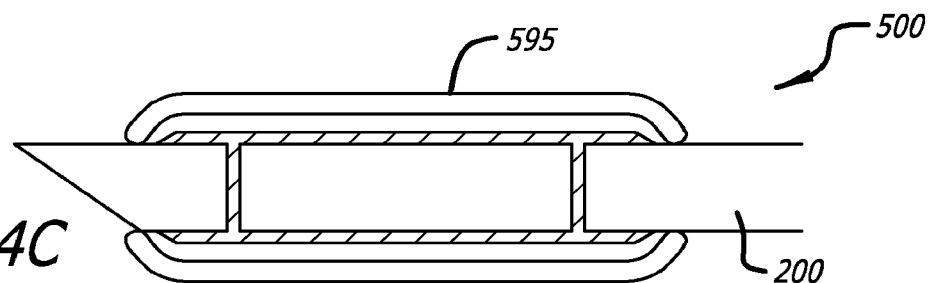
Figure 24D:
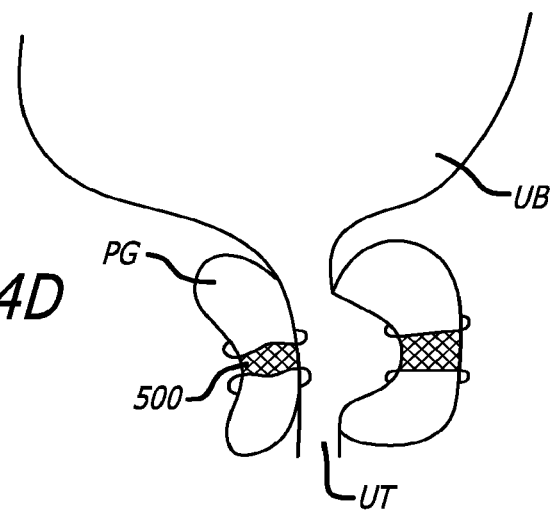

With regard to FIGS. 24A-D, in some aspects implant 500 includes mesh structure 551 and anchor tips 553. Mesh structure 551 is capable of reducing in length as it expands and lengthen as it is compressed. Anchor tips 553 have a preformed shape that is capable of providing an anchoring feature, as is depicted in one aspect in FIG. 24B. Anchor tips 553 are capable of being reversibly deformed to remove the anchoring feature, an aspect of which is depicted in FIG. 24C. With regard to FIG. 24C, constraining member 595 is capable of compressing mesh structure 551 and reversibly deforming anchor tips 553. Constraining member 595 provides a low-profile for implant 500 and secures it against delivery needle 200. When the distal anchor tips 553 are positioned near the outer tissue planes of prostate gland PG, constraining member 595 may be moved proximally to unsheathe distal anchor tips 553. Distal anchor tips 553 regain their anchoring features and engage tissue. As constraining member 595 is further retracted, mesh structure 551 expands and shortens and proximal anchor tips 553 deploy against tissue. FIG. 24D depicts implant 500 providing compression to prostate gland PG according to aspects described herein. In these aspects, implant 500 can be formed from a shape memory material, such as the metals or plastics described herein or their equivalents. In these aspects, the cross-sectional profile of mesh structure 551 can be round or flat. Further, to the extent deploying mesh structure 551 creates and temporarily preserves a void within prostate gland PG, such a void can be filled with suitable biocompatible adhesives or other permanent, porous, resorbable, and/or ingrowth-promoting materials.

Accordingly, the present invention contemplates both pushing directly on anchor portions of an anchor assembly as well as pushing directly upon the connector of the anchor assembly. Moreover, as presented above, the distal or first anchor component can be advanced and deployed through a needle assembly and at least one component of the proximal or second anchor component is advanced and deployed from the needle or from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Once implanted, the anchor assembly of the present invention accomplishes desired tissue manipulation, approximation, compression or retraction as well as cooperates with the target anatomy to provide an atraumatic support structure. In one preferred embodiment, the shape and contour of the anchor assembly is configured so that the assembly invaginates within target tissue, such as within folds formed in the urethra by the opening of the urethra lumen by the anchor assembly. In desired placement, wispy or pillowy tissue in the area collapses around the anchor structure. Eventually, the natural tissue can grow over the anchor assembly and new cell growth occurs over time. Such cooperation with target tissue facilitates healing and avoids unwanted side effects such as calcification or infection at the interventional site.

Subsequent to the interventional procedure, the patient can be directed to take appropriate drugs or therapeutic agents, such as alpha blockers and anti-inflammatory medicines.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector can for example, be coated with a polymer matrix or gel coating that retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors that can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and simultaneously remove the second anchor previously implanted for example, in the patient's urethra using electrosurgical, surgical or laser surgical devices used in performing transurethral prostate resection.

An aspect that the various embodiments of the present invention provide is the ability to deliver an anchor assembly having a customizable length, each anchor assembly being implanted at a different location without having to remove the device from the patient. Other aspects of the various embodiments of the present invention are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism that pulls on the anchor while the needle assembly is retracted.

It is to be recognized that various materials are within the scope of the present invention for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A method for treating benign prostatic hyperplasia, comprising:
    inserting an elongate device longitudinally through a urethra of a subject until at least a distal portion of the elongate device reaches a prostatic urethra; and
    deploying an expandable implant through a distal opening of the elongate device and between lateral lobes of a prostate gland, wherein deploying the expandable implant causes it to expand between the lateral lobes, and engage at least one anatomical feature at or near a distal end of the urethra without piercing the urethra or prostate gland, and compress at least a portion of the prostate gland,
    wherein at least a portion of the expandable implant comprises a shape-memory material defining one or more pre-formed curvatures, overlapping portions, or spirals.

2. The method of claim 1, wherein the shape-memory material comprises Nitinol.

3. The method of claim 1, wherein the elongate device comprises an introducer sheath defining an inner lumen configured to receive a compressed configuration of the expandable implant.

4. The method of claim 3, wherein the elongate device is flexible and configured to deflect laterally within the urethra.

5. The method of claim 1, wherein the elongate device further comprises an imaging modality.

6. The method of claim 5, wherein the imaging modality comprises an endoscope.

7. The method of claim 1, further comprising removing the expandable implant from the subject by retracting the expandable implant proximally through the urethra.

8. The method of claim 1, wherein the expandable implant is resorbable or degradable.

9. The method of claim 1, wherein the expandable implant comprises at least one pre-formed wire.

10. The method of claim 1, wherein a proximal portion of the expandable implant is coupled with a push rod.

11. The method of claim 1, wherein the expandable implant remains temporarily implanted in the prostatic urethra by engaging an inner wall of the urethra.

12. The method of claim 1, wherein the expandable implant remains temporarily implanted in the prostatic urethra by the engagement of the at least one anatomical feature at or near a distal end of the urethra.

13. The method of claim 12, wherein the at least one anatomical feature comprises a bladder neck.

14. The method of claim 1, further comprising rotating the expandable implant within the prostatic urethra after deploying the expandable implant between the lateral lobes of the prostate gland.

15. The method of claim 1, wherein the expandable implant is configured to be reversibly compressed.

16. The method of claim 1, wherein the expandable implant is configured to reduce in length as it expands and lengthen as it is compressed.

17. The method of claim 1, wherein deploying the expandable implant comprises withdrawing the elongate device from the prostatic urethra.

18. The method of claim 1, wherein at least a portion of the expandable implant is coated or embedded with one or more therapeutic substances or drugs.

19. The method of claim 18, wherein the one or more therapeutic substances or drugs comprise one or more phytochemicals, adrenergic receptor blocking agents, smooth muscle relaxants, bacteriostatic agents, analgesics, antibiotics, cancer treatment substances, or agents configured to inhibit a conversion of testosterone to dihydrotestosterone.

20. The method of claim 1, wherein at least a portion of the expandable implant is coated or embedded with one or more diagnostic substances.

* * * * *